US010816520B2

(12) United States Patent
Kasten et al.

(10) Patent No.: US 10,816,520 B2
(45) Date of Patent: Oct. 27, 2020

(54) GAS ANALYSIS SYSTEM

(71) Applicant: General Electric Company, Schenectady, NY (US)

(72) Inventors: Ansas Matthias Kasten, Schenectady, NY (US); William Albert Challener, Glenville, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 45 days.

(21) Appl. No.: 16/215,290

(22) Filed: Dec. 10, 2018

(65) Prior Publication Data

US 2020/0182842 A1 Jun. 11, 2020

(51) Int. Cl.
*G01N 33/00* (2006.01)
*G01N 21/31* (2006.01)
*G05D 1/00* (2006.01)

(52) U.S. Cl.
CPC ......... *G01N 33/0027* (2013.01); *G01N 21/31* (2013.01); *G05D 1/0094* (2013.01)

(58) Field of Classification Search
CPC ........... G01N 33/0027; G01N 33/0031; G01N 21/31; G05D 1/0094
See application file for complete search history.

(56) References Cited

U.S. PATENT DOCUMENTS

| 7,075,653 B1 | 7/2006 | Rutherford |
| 8,269,171 B2 | 9/2012 | Gorin |
| 10,113,956 B1 | 10/2018 | Li et al. |
| 2011/0082649 A1 | 4/2011 | Riti |
| 2013/0321637 A1 | 12/2013 | Frank et al. |

(Continued)

FOREIGN PATENT DOCUMENTS

| CN | 105805560 B | 10/2017 |
| KR | 191648674 B1 | 8/2016 |
| KR | 20180036299 A | 4/2018 |

OTHER PUBLICATIONS

Frish, Michael B., et al.; "Standoff and Miniature Chemical Vapor Detectors Based on Tunable Diode Laser Absorption Spectroscopy", IEEE Sensors Journal, vol. 10, Issue: 3, pp. 639-646, Mar. 2010.

(Continued)

*Primary Examiner* — Hina F Ayub
(74) *Attorney, Agent, or Firm* — Fletcher Yoder, P.C.

(57) ABSTRACT

A gas analysis system includes a scanning platform configured to direct a plurality of light beams over a target area. The scanning platform includes emitter spectroscopy assembly configured to emit the plurality of light beams toward respective target surfaces of the target area, receive a plurality of reflected light beams from the respective target surfaces, and determine a spectral intensity of each reflected light beam of the plurality of reflected light beams. Moreover, the scanning platform includes a main controller receive the feedback from the spectroscopy assembly indicative of the spectral intensity of each reflected light beam of the plurality of reflected light beams and determine a volumetric characterization of a gas plume based at least in part on the spectral intensity of a reflected light beam of the plurality of reflected light beams.

17 Claims, 13 Drawing Sheets

(56) References Cited

U.S. PATENT DOCUMENTS

| | | | |
|---|---|---|---|
| 2015/0006018 A1* | 1/2015 | Tesanovic | G08G 1/015 |
| | | | 701/29.6 |
| 2016/0214715 A1 | 7/2016 | Meffert | |
| 2017/0097274 A1 | 4/2017 | Thorpe et al. | |
| 2017/0284887 A1 | 10/2017 | Miranda | |
| 2018/0111683 A1* | 4/2018 | Di Benedetto | B64F 1/007 |
| 2018/0188129 A1* | 7/2018 | Choudhury | G01N 21/3504 |
| 2019/0003918 A1* | 1/2019 | Li | G01N 33/0027 |
| 2019/0064028 A1* | 2/2019 | Huang | G01N 21/85 |

OTHER PUBLICATIONS

Frish, Mchael B., et al.; "Low-cost lightweight airborne laser-based sensors for pipeline leak detection and reporting", Proceedings vol. 8726, Next-Generation Spectroscopic Technologies VI; 87260C (2013), Baltimore, May 29, 2013.

Bretschneider, Timo Rolf, et al.; "UAV-based gas pipeline leak detection", Asian Conference on Remote Sensing, Asian Conference on Remote Sensing, Myanmar, Oct. 2014.

PCT/US2019/065066; International Search Report and Written Opinion dated Mar. 30, 2020; 14 pages.

\* cited by examiner

GAS ANALYSIS SYSTEM

TECHNICAL FIELD

The subject matter disclosed herein relates to gas analysis systems. Specifically, embodiments of the present disclosure relate to techniques for detecting a gas plume, characterizing the gas plume, and/or determining a flow rate of a gas generating the gas plume.

BACKGROUND

This section is intended to introduce the reader to various aspects of art that may be related to various aspects of the present disclosure, which are described below. This discussion is believed to be helpful in providing the reader with background information to facilitate a better understanding of the various aspects of the present disclosure. Accordingly, it should be understood that these statements are to be read in this light, and not as admissions of prior art.

Gas infrastructure (e.g., pipelines, well pads, etc.) incur wear over time as a result of pressures at which gas is transported and stored, weather conditions, and/or other factors. Accurate gas detection is useful to maintain efficient operation of the gas infrastructure. Moreover, providing additional characterization data (e.g., gas type, gas plume concentration, gas flow rate, etc.) may aid in determining a corrective action upon detection of a gas. However, the gas infrastructure may span a wide area making it difficult to determine a source of gas and/or whether gas is present at a particular location.

BRIEF DESCRIPTION

In one embodiment, a gas analysis system includes a scanning platform configured to direct one or more light beams over a target area. The scanning device includes a spectroscopy assembly configured to emit the one or more light beams toward respective target surfaces of the target area, receive a plurality of reflected light beams from the respective target surfaces, and determine a spectral intensity of each reflected light beam of the plurality of reflected light beams. Moreover, the scanning platform includes a main controller configured to receive feedback from the spectroscopy assembly indicative of the spectral intensity of each reflected light beam of the plurality of reflected light beams and determine a volumetric characterization of a gas plume based at least in part on the spectral intensity of a reflected light beam of the plurality of reflected light beams.

In another embodiment, a gas analysis system includes an unmanned aerial vehicle configured to travel along a flight path. The unmanned aerial vehicle includes a spectroscopy assembly configured to emit one or more light beams toward respective target surfaces, receive a plurality of reflected light beams, and output a spectral intensity of each reflected light beam of the plurality of light reflected beams. Moreover, the unmanned aerial vehicle includes a thermal imager configured to capture one or more thermal images along the flight path. Additionally, the unmanned aerial vehicle includes a supplemental sensor configured to detect the wind condition at the unmanned aerial vehicle. Further, the unmanned aerial vehicle includes a main controller configured to determine a location of a gas plume based at least in part on the one or more thermal images. The main controller is configured to determine a volumetric characterization of the gas plume based at least in part on the spectral intensity of a reflected light beam of the plurality of reflected light beams and the wind condition.

In a further embodiment, a method includes the step of emitting one or more light beams toward a plurality of target surfaces. Each light beam of the one or more light beams reflects from a respective target surface of the plurality of target surfaces to generate a plurality of reflected light beams. The method also includes the step of receiving the plurality of reflected light beams. Moreover, the method includes the step of detecting a spectral intensity of each reflected light beam of the plurality of reflected light beams. Further, the method includes the step of determining a volumetric characterization of a gas plume based at least in part on of the spectral intensity of a reflected light beam of the plurality of reflected light beams.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Typical gas analysis systems and methods may be configured to emit a light beam to detect a species of gas (e.g., tunable diode light beam absorption spectroscopy, etc.). A gas analysis system may emit a light beam having a same wavelength of an absorption line of the species of gas that the gas detection system is configured to detect. As used herein, light beams refer to electromagnetic radiation that may include a wavelength between ten nanometers and one thousand meters. Accordingly, the light beams may include non-visible light (e.g., ultraviolet light, infrared light, or microwaves) and/or visible light. Further, the light beams may include both organized beams of light energy that travel along a substantially linear path as well as diffused light energy that may include unorganized light energy that travels along a non-linear path. The gas analysis system may be configured to receive the transmitted or reflected light beam to determine whether the species of gas is present. Traditional gas analysis systems may have low signal to noise ratios, which may lead to poor accuracy of gas detection. As such, traditional gas analysis systems may require increased scan/detection times to increase accuracy of the gas detection.

The systems and methods described herein relate to a gas analysis system configured to emit one or more light beams toward a target surface, which may achieve a higher signal to noise ratio for detecting and characterizing gas and/or permit faster scan rates than traditional systems. Further, the gas analysis system may be configured to scan for multiple types of gases simultaneously, scan a larger target area, determine a shape of a gas plume (e.g., two-dimensional shape, three-dimensional shape or a volumetric classification), and/or determine gas concentration levels of the gas plume (e.g., a gas concentration profile). Accordingly, the gas analysis system described herein may provide for quicker and/or more accurate detection of gas plumes than traditional gas detection systems, as well as provide additional information about the gas plume such as the shape and concentration profile.

Figure 1:
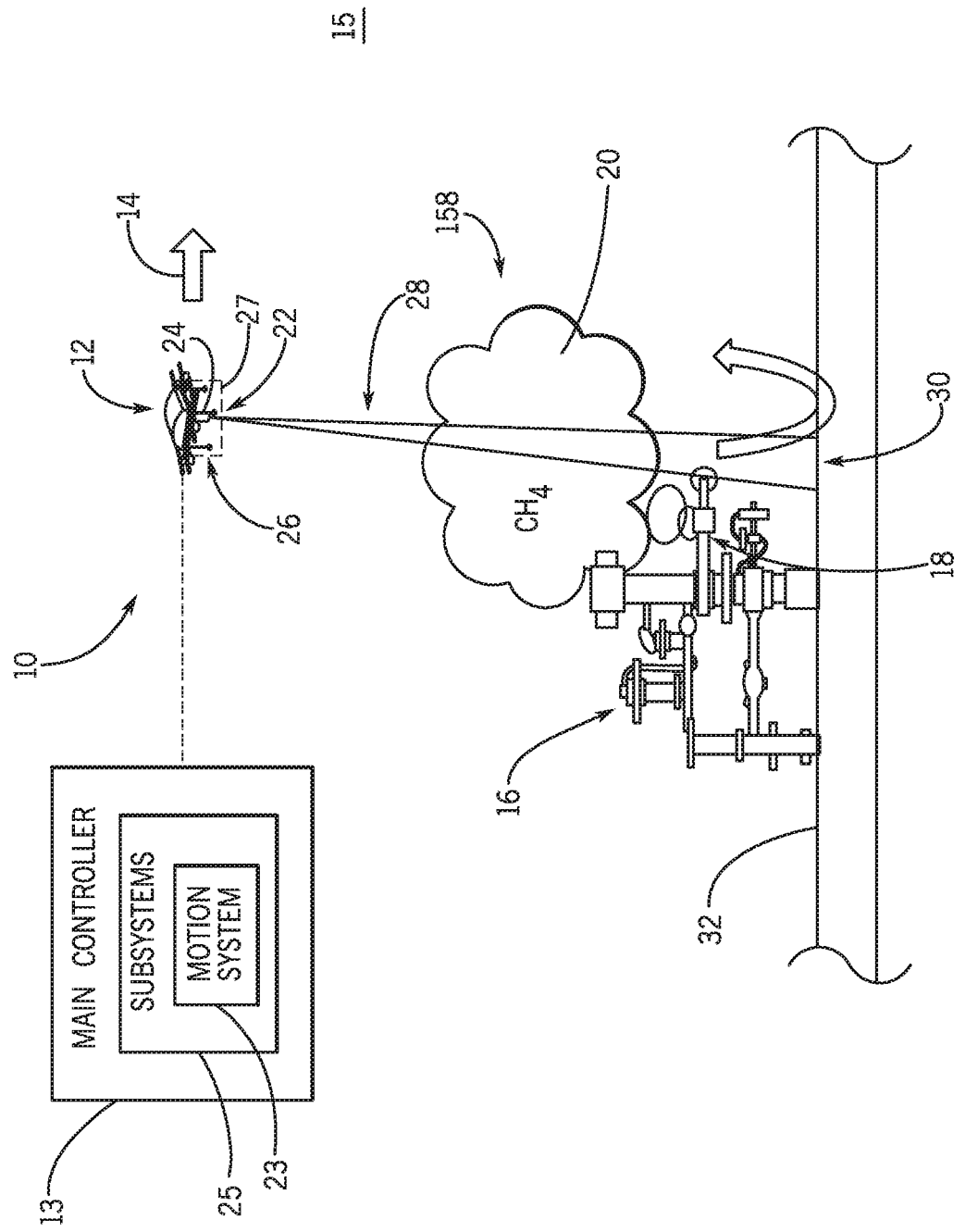
FIG. 1 is an elevation view of an embodiment of a gas analysis system having a scanning platform, in accordance with an aspect of the present disclosure.

FIG. 1 is an elevation view of an embodiment of a gas analysis system 10, in accordance with aspects of the present disclosure. In some embodiments, the gas analysis system 10 includes a scanning platform that includes components configured to analyze a given area for a target fluid. For example, the scanning platform may include an unmanned aerial vehicle 12, a manned aerial vehicle, an unmanned vehicle, a manned vehicle, an automobile, a stationary structure with movable actuators, and/or any other suitable structure or device that includes a motion system capable of directing emitters over the given area. While the present discussion focuses on the scanning platform including the unmanned aerial vehicle 12, it should be recognized that the scanning platform may include any suitable device. Therefore, the scanning platform is configured to direct and/or carry a spectroscopy assembly 22 for detecting and analyzing the target fluid (e.g., a gas).

In some embodiments, the scanning platform may include a main controller 13 configured to control movement of scanning platform via instructions output to a motion system 23 (e.g., a motor, an engine, an actuator, at least one propeller, a steering system, a braking system, landing gear, gimbal motion stabilizer, or other suitable systems) of the scanning platform. Furthermore, the main controller 13 is communicatively coupled to one or more subsystems 25 that may be utilized to provide feedback indicative of the target fluid, a position of the scanning platform, conditions of an environment 15 surrounding the area being analyzed, and/or other parameters. The subsystems 25 may also include sub control systems, such as the motion system 23. While the subsystems 25 are included within the main controller 13 in FIG. 1, it should be recognized that the subsystems 25 may be separate control systems that are communicatively coupled to the controller 13 wirelessly or via a wired connection. In some embodiments, the gas analysis system 10 includes an unmanned vehicle (e.g., the unmanned aerial vehicle 12 or an inspection drone) as the scanning platform. The unmanned aerial vehicle 12 may be configured to move along a travel path 14 (e.g., a flight path) within an environment 15 in which gas may be detected based at least in part on instructions output from the main controller 13. The flight path 14 may direct the unmanned aerial vehicle 12 to travel along a pipeline, a well pad 16, and/or another component that may transport or store a gas. The unmanned aerial vehicle 12 may be configured to detect a location 18 of the well pad 16 that may supply gas into the environment 15.

As shown in the illustrated embodiment of FIG. 1, the unmanned aerial vehicle 12 may be directed over a gas plume 20 that forms around the location 18 of the well pad 16. In some embodiments, the gas analysis system 10 includes the spectroscopy assembly 22 coupled to the unmanned aerial vehicle 12 so that the spectroscopy assembly 22 may obtain data as the vehicle travels along the flight path 14. Components of the spectroscopy assembly 22 are coupled to a spectroscopy assembly housing 24, and the spectroscopy assembly housing 24 may be coupled or mounted to the unmanned aerial vehicle 12. In the present embodiment, the spectroscopy assembly housing 24 is coupled to a bottom portion 26 of the unmanned vehicle 12. In other embodiments, the spectroscopy assembly housing 24 may be coupled to any suitable portion of the unmanned vehicle 12. In another embodiment, the spectroscopy assembly housing 24 may be coupled to the gimbal motion stabilizer 27 mounted to the unmanned vehicle 12. The spectroscopy assembly 22 may be configured to emit one or more light beams 28 toward respective target surfaces 30 to detect gas. In the depicted example the respective target surfaces 30 are located on a ground surface 32 below the gas plume 20. As the unmanned vehicle 12 travels along the flight path 14, the one or more light beams 28 reflect off the target surfaces 30 back toward the spectroscopy assembly 22. The spectroscopy assembly 22 may then detect the gas plume 20 based on a spectral intensity of the reflection of the light beams 28 that pass through the gas plume 20. As used herein, the spectral intensity refers to a radiant intensity per unit of frequency or wavelength.

In some embodiments, the spectroscopy assembly 22 may be configured to determine whether a specific type of gas is present in the gas plume 20, such as based on the absorption or transmission of the one or more light beams 28 through the gas plume. For example, the spectroscopy assembly 22 may be configured to emit a light beam 28 having a wavelength that is specific to an absorption of the specific type of gas. Different types of gases may have different absorption frequencies. As such, the light beam 28 having a specific wavelength and passing through the specific type of gas may be reflected from the target surface 30 with a reduced spectral intensity that may be detected by the spectroscopy assembly 22. In some cases, the wavelength of the light beam 28 may not be absorbed by other types of gas, such that the spectroscopy assembly 22 may detect the specific type of gas as a result of receiving reflected light that includes a spectral intensity that is below a threshold level.

In some embodiments, the spectroscopy assembly 22 is configured to tune the light beam 28 over a range of wavelengths. The range of wavelengths may be centered around an absorption line of a specific type of gas. The absorption line may include at least one absorption frequency of the specific type of gas. The range of wavelengths may include the wavelength corresponding to the absorption line, wavelengths above the absorption line, and wavelengths below the absorption line. Tuning the light beam to include the range of wavelengths may provide verification data to the spectroscopy assembly. For example, a first light beam may be emitted at a first wavelength corresponding to a wavelength of the absorption line and a second light beam may be emitted at a second wavelength corresponding to a wavelength above the absorption line. A drop in spectral intensity of the first light beam, but not the second light beam may provide verification data indicating that the light beam passed through the specific type of gas. However, a drop in the spectral intensity of both the first light beam and the second light beam may provide verification data indicating that another substance or object (e.g., another type of gas, ground surface, etc.) may be absorbing the first and second light beams.

Additionally or alternatively, the spectroscopy assembly 22 is configured to determine a shape 158 of the gas plume 20. Further, in some embodiments, the spectroscopy assembly 22 is configured to determine a concentration of gas within a portion or throughout the gas plume 20 (e.g., determine a concentration profile of the gas plume 20). Further still the spectroscopy assembly 22 may be configured to determine a flow rate of gas from the location 18 into the environment 15.

Figure 2:
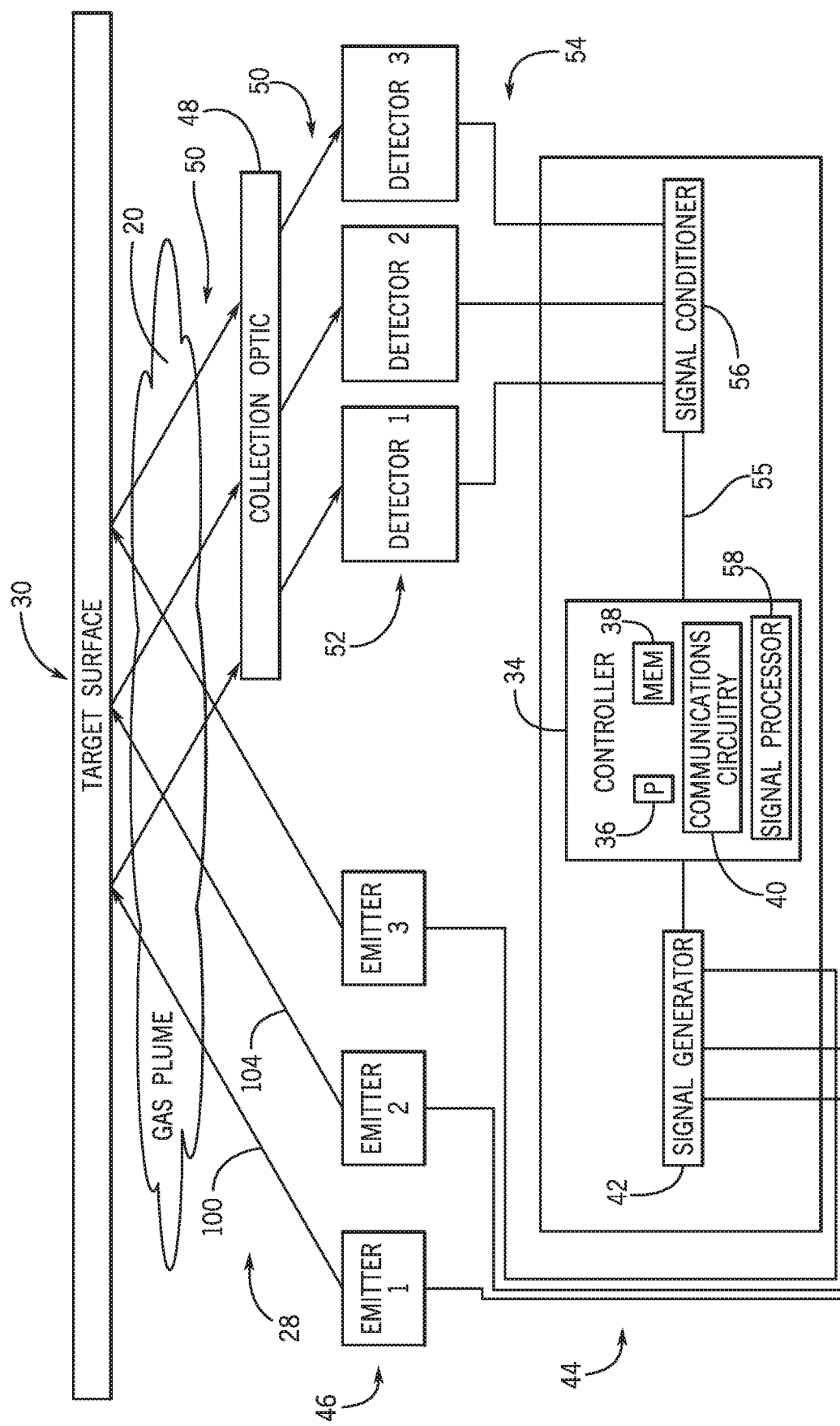
FIG. 2 is a block diagram of an embodiment of a spectroscopy assembly of the gas analysis system, in accordance with an aspect of the present disclosure.

FIG. 2 is a block diagram of an embodiment of the spectroscopy assembly 22 of the gas analysis system 10. In some embodiments, the spectroscopy assembly 22 includes a controller 34 comprising an application specific integrated circuit (ASIC) or a processor 36 and a memory device 38. The memory device 38 may be configured to store instructions executable by the processor 36 to perform the methods and to control actions described herein. For example, the processor 36 may execute instructions stored on the memory device 38 to control a signal generator 42 based on inputs indicating that the unmanned vehicle 12 is disposed proximate a target location within the environment 15. The memory device 38 may also be configured to store data received during analysis of the target location.

As shown in the illustrated embodiment of FIG. 2, the controller 34 may include communications circuitry 40, such as antennas, radio transceiver circuits, signal processing hardware and/or software (e.g., hardware or software filters, A/D converters, multiplexers, amplifiers), or a combination thereof. The communications circuitry 40 may be configured to communicate over wired (e.g., serial ports: UART, RS-232, RS-485, CAN bus, SPI, I2C, Ethernet, USB, etc.) or wireless communication paths (e.g., IR wireless communication, satellite communication, broadcast radio, microwave radio, Bluetooth, Zigbee, Wifi, UHF, NFC, etc.). Such communication may also include intermediate communication devices, such as radio towers, cellular towers, etc. In some embodiments, the controller 34 of the spectroscopy assembly 22 may be configured to communicate with the main controller 13 (shown in FIG. 4) of the unmanned vehicle 12 via the communications circuitry 40. For example, the controller 34 may output a data signal indicative of the data (e.g., a change in spectral intensity of each of a plurality of light beams 28) received during inspection of the target location to the main controller 13 over a wireless network via the communications circuitry 40. In some embodiments, the main controller 13 may utilize the signal to adjust the flight path 14 and/or perform another suitable action.

As set forth above, the spectroscopy assembly 22 may be configured to determine a specific type of gas or gases that are present in the gas plume 20. Thus, the spectroscopy assembly 22 may be configured to cause light sources to emit one or more light beams 28 having respective wavelengths that are specific to the absorption frequencies for one or more target gases. The spectroscopy assembly 22 may include a signal generator 42 configured to generate a light beam signal 44 having the wavelength that is specific to the absorption frequency of a target gas. In some embodiments, the signal generator 42 may be configured to generate a plurality of light beam signals 44. The signal generator 42 may generate each light beam signal 44 of the plurality of light beam signals 44 to have a respective wavelength corresponding to an absorption frequency of a target gas based on instructions received from the controller 34. As such, each light beam signal 44 of the plurality of light beam signals 44 may have a different wavelength. The signal generator 42 may output the plurality of light beam signals 44 to a plurality of light beam emitters 46 that generate the plurality of light beams 28. In some embodiments, the signal generator 42 may be configured output each light beam signal 44 of the plurality of light beam signals 44 to a respective light beam emitter 46 of the plurality of light beam emitters 46.

The plurality of light beam emitters 46 may be configured to emit each respective light beam 28 of the plurality of light beams 28 toward a respective target surface 30 (or to a common target surface 30). In some embodiments, each light beam emitter 46 of the spectroscopy assembly 22 may include at least one light beam diode (e.g., a light emitting diode) configured to generate the light beam in response to the light beam signal 44. Each light beam emitter 46 may also include a focusing lens configured to focus the light beam 28 generated by the light beam diode. In some embodiments, the focusing lens is oriented such that the light beam 28 is directed through the focusing lens toward a respective target surface 30. Each light beam 28 of the plurality of light beams 28 may reflect off of the respective target surface 30 in a direction toward a collection optic 48 of the spectroscopy assembly 22. The collection optic 48 may receive reflected light beams 50 reflected from the respective target surfaces 30. Specifically, the reflected light beams 50 may pass through the collection optic 48, which may focus the reflected light beams 50 onto at least one detector 52 (e.g., photo detector) of the spectroscopy assembly 22.

In some embodiments, the at least one detector 52 is configured to detect the reflected light beam 50. In some embodiments, a single detector 52 is configured to detect a plurality of reflected wavelengths. In other embodiments, the spectroscopy assembly 22 includes a plurality of detectors 52, where each detector 52 is configured to detect a respective emitted wavelength. For instance, the spectroscopy assembly 22 may include a detector 52 corresponding to each emitted wavelength. The at least one detector 52 may output a reflected light beam signal 54 based at least in part on the reflected light beam 50 detected by the at least one detector 52. The reflected light beam signal 54 may be based at least in part on a spectral intensity, wavelength, frequency, directionality, another suitable parameter, or any combination thereof of the reflected light beam 50 detected by the detector 52. In some embodiments, the spectroscopy assembly 22 includes a signal conditioner 56 configured to receive the reflected light beam signal 54 which may be an analog signal. The signal conditioner 56 may be configured to process or condition (e.g., pre-amplify, filter, etc.) the reflected light beam signal 54 and convert the reflected light beam signal 44 into a digital reflected light beam signal 55. In some embodiments, the signal conditioner 56 may consolidate multiple reflected light beam signals 54 into a single digital reflected light beam signal 55 that is received by the controller 34. In other embodiments, the signal conditioner 56 may send individual digital reflected light beam signals 55 to the controller 34 that correspond to each of the reflected light beam signals 54. The signal conditioner 56 may send a plurality of digital reflected light beam signals 55 to the controller 34 simultaneously or send the signals in series.

In some embodiments, the controller 34 is configured to receive the digital reflected light beam signal 55. The controller 34 may be configured to analyze and post-process the digital reflected light beam signal 55. In some embodiments, the controller 34 includes a digital lock-in amplifier configured to analyze the digital reflected light beam signal 55. In some embodiments, the controller 34 may include an analog mixer or demodulator to analyze the digital reflected light beam signal 55. Additionally or alternatively, the controller 34 may include a signal processor 58 (e.g., a digital signal processing unit) configured to post-process the digital reflected light beam signal 55. The controller 34 may be configured to determine a change in spectral intensity of the light beam from emission at the light beam emitter to detection at the detector 52 based at least in part on the analysis and post-processing of the digital reflected light beam signal 54. A change in spectral intensity of the light beam may indicate that the light beam passed through a gas plume 20 of a type of gas configured to be detected by the light beam. Thus, the spectroscopy assembly 22 may be configured to detect gas based at least in part on a change in spectral intensity of the respective light beams 28.

In some embodiments, the spectroscopy assembly 22 may be configured to detect multiple types of gases. For example, the controller 34 may be configured to determine that a first type of gas present in the gas plume 20 based at least in part on the change in spectral intensity of a first light beam 100 having a first wavelength relevant to the measurement of the first type of gas. For example, the first light beam 100 may have a wavelength corresponding to an absorption frequency of the first target gas. Further, the controller 34 may be able to determine a second target gas that is present in the gas plume 20 based at least in part on the change in spectral intensity of a second light beam 104 having a different wavelength relevant to the measurement of the second type of gas. The second light beam 104 may have a wavelength corresponding to an absorption frequency of the second target gas. The first light beam 100 may be emitted from a first light beam emitter 46 and the second light beam 104 may be emitted from a second light beam emitter 46 in order to facilitate emission of the different wavelengths. However, in some embodiments, a single light beam emitter may be configured to output a plurality of light beams 28 (e.g., the first and second light beams 100, 104) at different wavelengths.

In some embodiments, the spectroscopy assembly 22 may be configured to detect multiple target gases using a single light beam emitter that is configured to output a tunable light beam. For example, the spectroscopy assembly 22 may include a tunable diode light beam absorption spectroscopy ("TDLAS") sensor. The spectroscopy assembly 22 may include a tunable diode that tunes the tunable light beam to a plurality of target wavelengths based at least in part on instructions from the controller 34. The spectroscopy assembly 22 may adjust the temperature of the tunable diode to cause the tunable diode to emit the tunable light beam having the plurality of target wavelengths. However, any suitable adjustment technique may be used to adjust the tunable diode. The detector 52 may be configured to receive the reflected tunable light beam and separate or otherwise distinguish the individual beams of the tunable light beam. As such, the spectroscopy assembly 22 may be configured to determine changes in spectral intensity of the tunable light beam for each wavelength of the plurality of target wavelengths. A change in spectral intensity of the tunable light beam at a wavelength of the plurality of target wavelengths may indicate that the tunable light beam passed through a gas plume 20 of a target gas associated with the wavelength. The spectroscopy assembly 22 may determine changes in spectral intensity at multiple wavelengths to detect multiple target gases using the single light beam emitter that outputs the tunable light beam.

Figure 3:
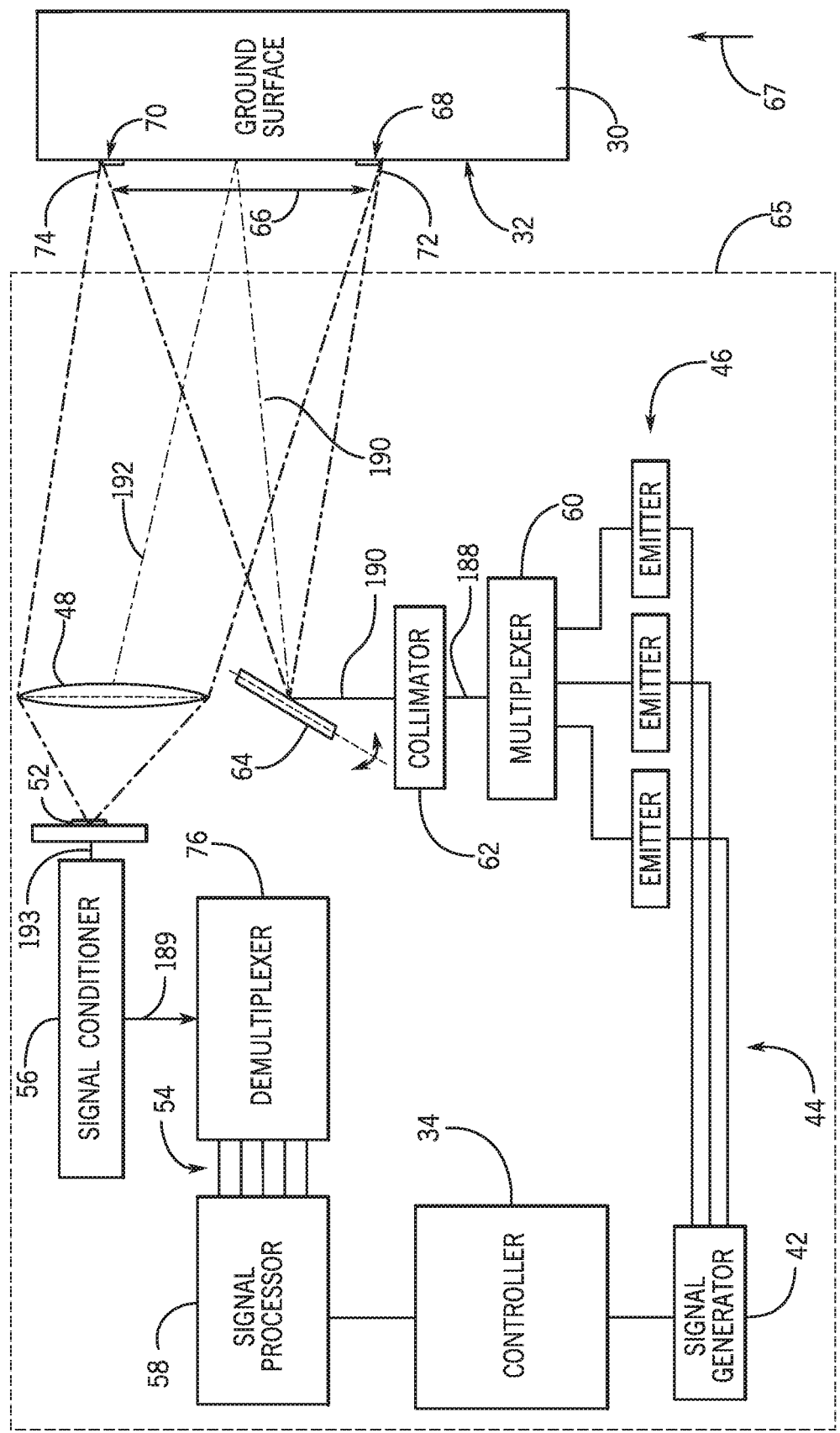
FIG. 3 is a block diagram of an embodiment of the spectroscopy assembly configured to multiplex light beam signals, in accordance with an aspect of the present disclosure.

FIG. 3 is a block diagram of an embodiment of the spectroscopy assembly 22 of FIG. 2 configured to multiplex the light beam signals 44. As set forth above, the spectroscopy assembly 22 includes the controller 34 configured to instruct the signal generator 42 to output the plurality of light beam signals 44. In the illustrated embodiment, the spectroscopy assembly 22 includes a multiplexer 60 (e.g., an optical fiber multiplexer) that receives the plurality of light beam signals 44 output from the emitters 46. The multiplexer 60 may be configured to combine the plurality of light beams 28 into a single light beam signal (e.g., multiplexed light beam signal 188) and output the multiplexed light beam signal 188. In some embodiments, the multiplexer 60 includes a light beam collimator 62 that may receive the multiplexed light beam signal 188 and output a multiplexed light beam 190. The light beam collimator 62 may be configured to collimate the multiplexed light beam signal 188 to generate the multiplexed light beam 190 by narrowing the multiplexed light beam signal 188 to align the multiplexed light beam signal 188 in a specific direction or to cause a spatial cross section of the multiplexed light beam signal 188 to become smaller. The light beam collimator 62 may then direct the multiplexed light beam 190 toward the target surface 30.

As shown in the illustrated embodiment of FIG. 3, the light beam collimator 62 is configured to direct the multiplexed light beam 190 toward a scanning micro-mirror 64. The multiplexed light beam 190 may reflect off of the scanning micro-mirror 64 toward the target surface 30. The scanning micro-mirror 64 may be configured to rotate with respect to a light beam sensor housing 65. Thus, the scanning-micro mirror 64 may be configured to direct the multiplexed light beam 190 toward the target surface 30. In some embodiments, the scanning micro-mirror 64 is configured to rotate to sweep (e.g., oscillate or otherwise move) the multiplexed light beam 190 along the ground surface 32. Sweeping the light beam may increase a scanning range 66 of the spectroscopy assembly 22 as the unmanned vehicle 12 travels along the flight path 14. For example, the multiplexed light beam 190 may be directed vertically downward toward the ground surface 32 as the unmanned vehicle 12 travels in an operating direction 67. Rotating the scanning micro-mirror 64 may direct the light beam between a left target surface 68 disposed on a left side of the scanning range 66 and a right target surface 70 disposed on a right side of the scanning range 66. Without rotating the scanning micro-mirror 64, the scanning range 66 of the spectroscopy assembly 22 may be reduced and include an area covered by one of the target surfaces 68, 70. Rotating or otherwise moving the scanning micro-mirror 64 may increase the scanning range 66 and enable the multiplexed light beam 190 to cover a larger surface area as the unmanned vehicle 12 is directed along the flight path 14. In some embodiments, the scanning micro-mirror 64 may include multiple degrees of movement (e.g., rotation about multiple axes) to enable the scanning micro-mirror 64 to direct the multiplexed light beam 190 toward the target surface 30.

The multiplexed light beam 190 may be configured to reflect off of the target surface 30 in a direction toward the collection optic 48. The reflected multiplexed light beam 192 may pass through the collection optic 48, and the collection optic 48 may focus the reflected multiplexed light beam 192 onto the at least one detector 52 of the spectroscopy assembly 22. The at least one detector 52 is configured to detect the reflected multiplexed light beam 192, and output a reflected multiplexed light beam signal 193 based at least in part on the reflected multiplexed light beam 192 detected by the at least one detector 52. The spectroscopy assembly 22 may include a signal conditioner 56 configured to receive the reflected multiplexed light beam signal 193, which may be an analog signal. The signal conditioner 56 is configured to process or condition (e.g., pre-amplify, filter, etc.) the reflected multiplexed light beam signal 193 and convert the reflected multiplexed light beam signal 193 into a digital reflected multiplexed light beam signal 189.

In some embodiments, the controller 34 is configured to receive the digital reflected multiplexed light beam signal 189 to analyze and post-process the digital reflected multiplexed light beam signal 189. In some embodiments, the controller 34 or the signal conditioner 56 includes a demultiplexer 76 configured to demultiplex the digital reflected multiplexed light beam signal 189 into a plurality of digital reflected light beam signals 54. As used herein, demultiplex may include separating a single signal (e.g., the digital reflected multiplexed light beam signal 189) into multiple separate signals. Accordingly, the demultiplexer 76 essentially reverses the process of the multiplexer 60. The controller 34 may be configured to determine a change in spectral intensity of each respective light beam of the plurality of digital reflected light beam signals 54. A change in spectral intensity of a respective light beam may indicate that the respective light beam passed through the gas plume 20 having a target gas configured to be detected by a corresponding light beam of the multiplexed light beam 190. Thus, the spectroscopy assembly 22 may be configured to detect gas based at least in part on a change in spectral intensity of a respective light beam of the multiplexed light beam 190. Moreover, the spectroscopy assembly 22 may be configured to detect multiple target gases based at least in part on a change in spectral intensity of respective light beams 28 of the multiplexed light beam 190.

Figure 4:
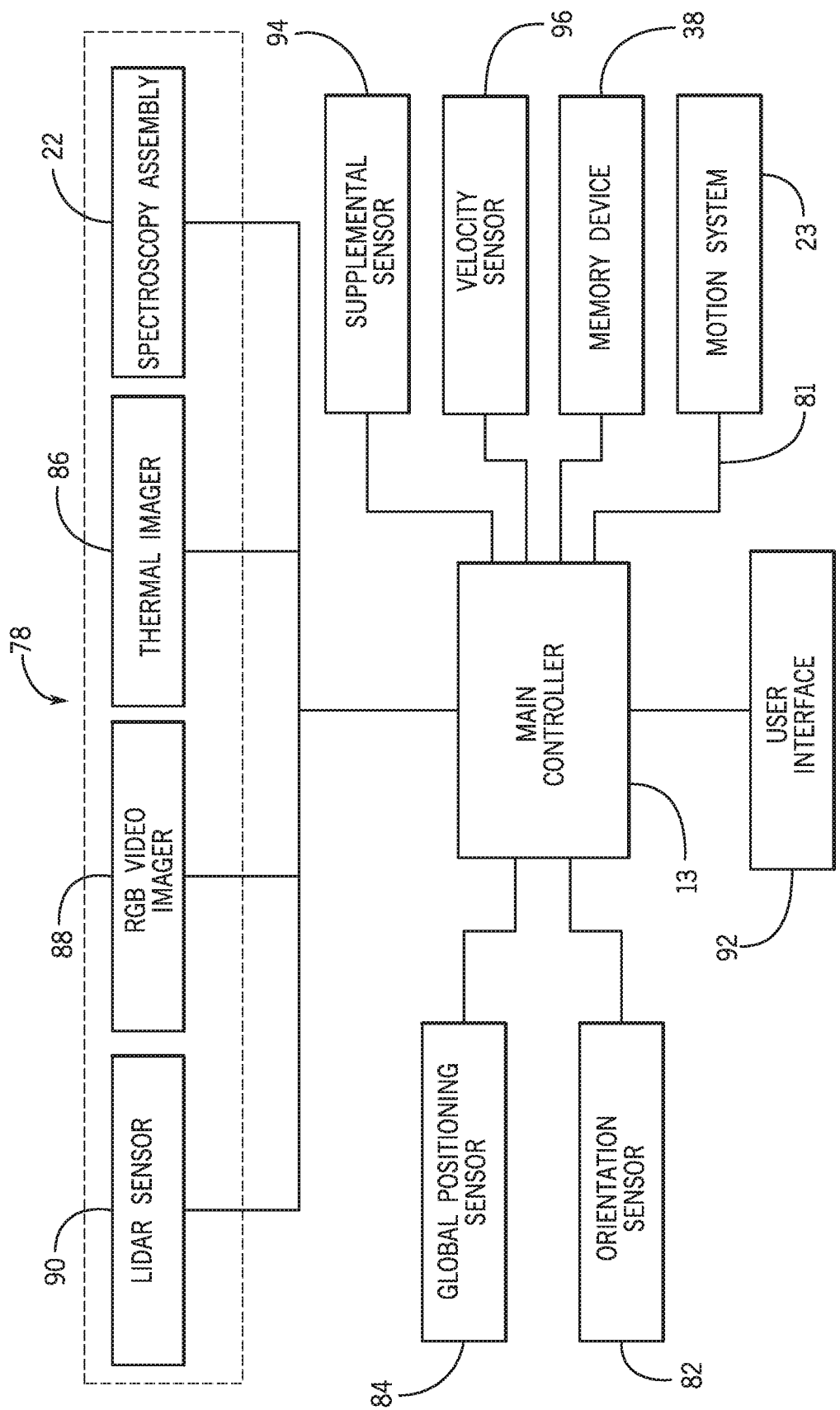
FIG. 4 is a block diagram of an embodiment of a platform control system, in accordance with an aspect of the present disclosure.

FIG. 4 is a block diagram of an embodiment of a platform control system 78 that may be included in the unmanned vehicle 12 or in another suitable scanning platform 12. The platform control system 78 (e.g., unmanned aerial vehicle control system) may include a main controller 13. The main controller 13 may be configured to control the unmanned vehicle 12 to execute the flight path 14. Specifically, the main controller 13 may be configured to output a motion control signal 81 to the motion system 23. As set forth above, the motion system 23 may include at least one propeller, at least one motor, an engine, an actuator, a steering system, a braking system, landing gear, or other suitable systems. The motion control signal 81 may include instructions to the motion system 23 that move the unmanned vehicle along the flight path 14. For example, the main controller 13 may be configured to output the motion control signal 81 to the motion system 23, where the motion control signal includes instructions to drive a propeller of the unmanned vehicle 12, such that the unmanned vehicle 12 travels along the flight path 14. The main controller 13 may be configured to control vehicle systems to maintain a desired height and/or speed of the unmanned vehicle 12. For example, the main controller 13 may be configured to instruct the unmanned vehicle 12 to lower its height and position the unmanned vehicle 12 closer to the target surface 32 upon detecting a target gas. In some embodiments, the main controller 13 is configured to cause the unmanned vehicle 12 to move with respect to a roll axis, a yaw axis, and/or a pitch axis to aim the plurality of light beams 28 emitted from the spectroscopy assembly 22 toward respective target surfaces 30. The platform control system 78 may include an orientation sensor 82 configured to detect an orientation (e.g., degrees of rotation about the roll axis, the yaw axis, and/or the pitch axis) of the unmanned vehicle 12 with respect to the ground surface 32 and the direction of travel 67 of the unmanned vehicle 12. The orientation sensor 82 may output the orientation of the unmanned vehicle 12 to the main controller 13

In some embodiments, the platform control system 78 includes a global positioning sensor 84 configured to detect a current location of the unmanned vehicle 12 along the flight path 14 and/or with respect to the ground surface 32. The main controller 13 may be configured to control the systems of the unmanned vehicle 12 based at least in part on a predetermined flight path 14 for the unmanned vehicle 12 and the current location of the unmanned vehicle 12. Moreover, the main controller 13 may tag data received from the spectroscopy assembly 22, a thermal imager 86, a video imager 88 (e.g., RGB video imager), or a light and detection ranging ("LIDAR") sensor 90 with the current location of the unmanned vehicle 12 and save geotagged data (e.g., the received data with the respective current location) on a vehicle memory device 38. The main controller 13 may be configured to output the geotagged data to a network, the controller 34, and/or another computing device.

In some embodiments, the LIDAR sensor 90 is configured to detect a topology, terrain, type, or other characteristic of the target surface 30 and/or the ground surface 32. For example, the LIDAR sensor 90 may detect that the ground surface 32 includes sand, grass, soil, rocks, gravel, or any combination thereof. The LIDAR sensor 90 may be configured to output data related to the target surface 30 and/or the ground surface 32 to the main controller 13. In some embodiments, the main controller 13 may determine a reflectivity of the target surface 30, and thus, adjust analysis parameters based on the determined reflectivity of the target surface 30. Further, the main controller 13 may be configured to adjust the flight path 14 based at least in part on the topology of the target surface 30.

In some embodiments, the main controller 13 is also configured to receive inputs from a user interface 92. The inputs from the user interface 92 may include instructions related to the flight path 14 and/or deviations from a previous flight path 14, which may be at least part of the motion control signal 81 to the motion system 23. Moreover, the main controller 13 may receive inputs related to target gases that may be detected within the environment 15. Accordingly, the main controller 13 may instruct the spectroscopy assembly 22 to output light beams at a specific wavelength corresponding to the target gases based on the inputs received from the user interface 92. In some embodiments, the controller 34 of the spectroscopy assembly 22 is configured to receive inputs directly from the user interface 92. In other embodiments, the main controller 13 is configured to output instructions to the spectroscopy assembly 22 and/or one or more other of the subsystems 25 based at least in part on inputs received from the user interface 92.

In some embodiments, the platform control system 78 includes the thermal imager 86 configured to capture a one or more thermal images of an area proximate the unmanned vehicle 12, such as the target surface 30. The thermal imager 86 may continuously capture thermal images as the unmanned vehicle 12 travels along the flight path 14. In other embodiments, the thermal imager 86 is configured to capture thermal images at a preset interval (e.g., every second, every 10 seconds, every 30 seconds, or every minute). Additionally or alternatively, the thermal imager 86 is configured to capture thermal images of specified objects, surfaces, and/or locations within the environment 15. For example, the thermal imager 86 may capture the one or more thermal images of the location 18 at which gas enters the environment 15. The thermal imager 86 is configured to output the thermal images to the main controller 13, which may determine that the gas plume 20 is present and/or analyze the gas plume 20 based on an analysis of the thermal images. For instance, the main controller 13 may determine a general shape and size of the gas plume 20, a temperature of the gas plume 20, a concentration distribution of the gas plume 20, or other characteristics of the gas plume 20 based on the thermal images received from the thermal imager 86.

In some embodiments, the platform control system 78 includes a red, green, blue ("RBG") video imager. The RGB video imager 88 may be configured to capture visual video images of the target surfaces proximate the gas plume 20. The RGB video imager 88 may output the visual video images to the main controller 13, and the main controller 13 may save the visual video images on the vehicle memory device 38. In some embodiments, the main controller 13 may analyze the visual video images to determine a condition of the location 18 where gas enters the environment 15. In other embodiments, the main controller 13 is configured to output the visual video images to the user interface 92 such that the user may analyze the visual video images and determine a condition of the location where gas enters the environment 15.

Moreover, the platform control system 78 may include the spectroscopy assembly 22. As set forth above, the spectroscopy assembly 22 may be configured to detect gas and/or a type of gas based at least in part on a change in spectral intensity of the light beam 28 emitted from the emitter 46 and reflected back to the detector 52 of the spectroscopy assembly 22. The controller 34 of the spectroscopy assembly 22 may be communicatively coupled to the main controller 13, and thus, the controller 34 may send feedback indicative of a detection of gas or a type of gas to the main controller 13. However, in other embodiments, the spectroscopy assembly 22 may be integrated into the platform control system 78 such that the spectroscopy assembly 22 does not include a dedicated or separate controller (e.g., the controller 34) and the main controller 13 functions as the controller for the spectroscopy assembly 22. For example, the signal generator 42 of the spectroscopy assembly 22 may generate each light beam signal 44 of the plurality of light beam signals 44 to have a specific wavelength based on instructions received from the main controller 13. Additionally, the main controller 13 may be configured to determine the type of gas present in the gas plume 20 based at least in part on the change in spectral intensity of a light beam 28 of the plurality of light beams 28. In some embodiments, the main controller 13 is also configured to analyze the gas plume 20 (e.g., determine the shape 158 or a concentration of the gas plume 20) based at least in part on changes in spectral intensity of the plurality of light beams 28.

In some embodiments, the platform control system 78 includes a supplemental sensor 94 (e.g., a flow sensor, an accelerometer, a piezoelectric sensor, or another suitable sensor) configured to detect a wind condition at a location of the unmanned vehicle 12. The supplemental sensor 94 may output a wind condition signal, indicating the wind condition, to the main controller 13. In some embodiments, the unmanned vehicle 12 may be above the gas plume 20 with respect to the ground surface 32, such that the wind condition may be different at the location of the unmanned vehicle 12 than the location of the gas plume 20. For example, the wind condition at the unmanned vehicle 12 may include wind blowing in a first direction at fifteen miles per hour ("mph"), and the wind condition at the gas plume 20 may include wind blowing in a second direction at twelve mph. Thus, in response to detecting the gas plume 20, the platform control system 78 may lower the height of the unmanned vehicle 12 toward the gas plume 20 to obtain a more accurate wind condition from the supplemental sensor 94. In other embodiments, the main controller 13 may be configured to receive the wind condition over a network (e.g., the Internet) and/or from another device external to the main controller 13 and the unmanned vehicle 12.

In some embodiments, the unmanned vehicle 12 includes a velocity sensor 96 configured to detect a velocity of the unmanned vehicle 12. The velocity sensor 96 may output a velocity signal indicative of the detected velocity to the main controller 13. The main controller 13 may be configured to determine an actual wind condition based at least in part on the wind condition signal from the supplemental sensor 94 and the velocity signal from the velocity signal 96.

In some embodiments, the main controller 13 may be configured to determine a gas flow rate from the location 18 directing gas into the environment 15 to form the gas plume 20 based at least in part on the actual wind condition, the shape 158 of the gas plume 20, and the concentration of the gas plume 20. For example, the main controller 13 may determine a gas flow rate based on a change in volume of the gas plume 13 in response to a signal indicative of the shape 158 of the gas plume 20 increasing in size (e.g., volume of the gas plume 20 increasing), a signal indicative of the gas concentration of the gas plume 20 remaining substantially constant, and a signal indicative of no actual wind condition (e.g., no wind is currently blowing).

Figure 5:
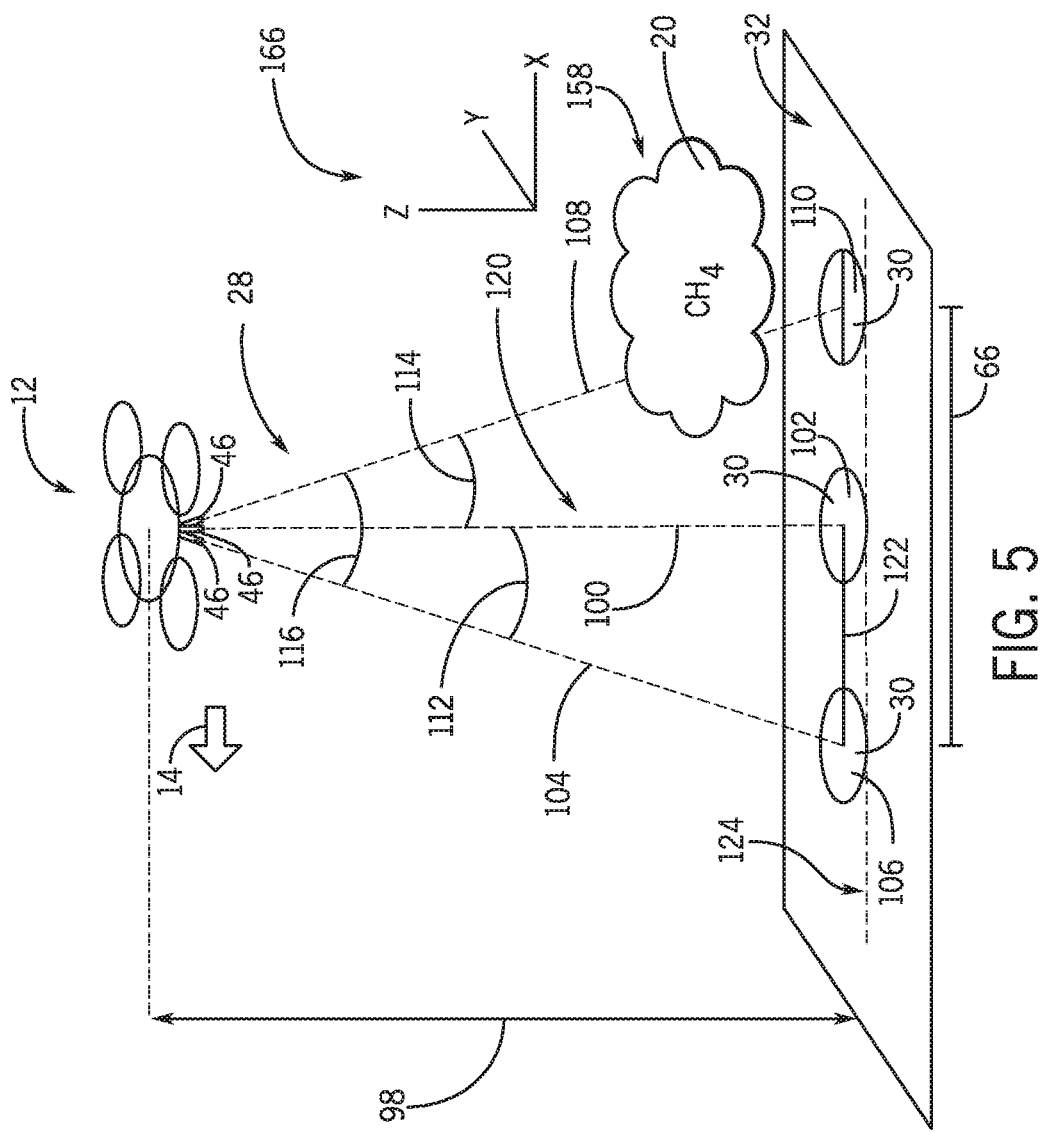
FIG. 5 is a view of an embodiment of the gas analysis system emitting one or more light beams, in accordance with an aspect of the present disclosure.

FIG. 5 is a perspective view of an embodiment of the gas analysis system 10 having the unmanned aerial vehicle (e.g., unmanned vehicle 12) emitting the plurality of light beams 28. The unmanned vehicle 12 may travel along the flight path 14 at a height 98 from the ground surface 32 based at least in part on the flight path 14. In some embodiments, the height 98 is between one foot and one hundred feet, between five feet and fifty feet, or between 3 feet and 15 feet above the ground surface 32. The height of the unmanned vehicle 12 may change as the unamend vehicle 12 moves along the flight path 14. In some embodiments, the height of the unmanned vehicle 12 may change along the flight path 14 based on the topology of the inspection area (e.g., the target surface 30) at specific points along the flight path 14. For example, in a wooded area with tall trees, the flight path 14 may cause the unmanned vehicle 12 to increase the height 98 such that the unmanned vehicle 12 maintains a minimum distance above the trees (e.g., the path of the unmanned vehicle 12 is unobstructed by the trees). In some embodiments, the flight path 14 may cause the height 98 of the unmanned vehicle 12 to move up and down based on the topology of the inspection area along the flight path 14 to maintain a constant height of the unmanned vehicle 12 with respect to the ground surface 32. Additionally or alternatively, the flight path 14 is based at least in part on the wind condition or other parameter affecting flight of the unmanned vehicle 12 or the scan. For example, a wind speed at fifty feet above the ground surface 32 may be thirty mph, and a wind speed twenty feet above the ground surface 32 may be ten mph. The main controller 13 may adjust the flight path 14 to lower the unmanned vehicle 12 to twenty feet above the ground to fly the unmanned vehicle 12 with a lower wind speed.

The unmanned vehicle 12 may include a plurality of light beam emitters 46 configured to emit each light beam 28 of a plurality of light beams 28 toward a respective target surface 30. As shown in the illustrated embodiment of FIG. 5, the plurality of light beam emitters 46 emits a first light beam 100 toward a first target surface 102, a second light beam 104 toward a second target surface 106, and a third light beam 108 toward a third target surface 110. Each light beam 100, 104, 108 of the plurality of light beams 28 may be emitted at a different angle with respect to the unmanned vehicle 12 (and/or the ground surface 32), such that each light beam 100, 104, 108 of the plurality of light beams 28 includes an angular offset from each other. For example, the first light beam 100 may be offset from the second light beam 104 by a first angle 112, the first light beam 100 may be offset from the third light beam 108 by a second angle 114, and the second light beam 104 and the third light beam 108 may be offset by a third angle 116.

In some embodiments, the first light beam 100 may be emitted directly downward (e.g., along a z-axis 166) by the plurality of light beam emitters 46 from the unmanned vehicle 12. As the first light beam 100 is emitted directly downward, a first height 120 from the spectroscopy assembly 22 to the first target surface 102 may be the height 98 of the unmanned vehicle 12 from the ground surface 32. For example, for an unmanned vehicle 12 flying at a height of ten feet, the first height 120 may be ten feet. As a non-limiting example, the first angle 112 (e.g., angle between the first light beam 100 and the second light beam 104) may be two degrees. Thus, a first distance 122 between the first target surface 102 and the second target surface 106 may be approximately (e.g., within 10% of, within 5% of, or within 1% of) four inches. Lowering the height of the unmanned vehicle 12 may increase a resolution of the scan, but decrease the scanning range 66. The resolution increases as the plurality of target surfaces 102, 106, 110 move closer together (e.g., decrease the first distance 122), but scanning range 66 also decreases as the target surfaces 102, 106, 110 move closer together. Thus, the unmanned vehicle 12 may control the scanning range 66 and the resolution of the scan based at least in part on the height 98 of the unmanned vehicle 12.

In some embodiments, the first angle 112 and then second angle 114 may be substantially equal. For example, the first angle 112 may be two degrees and the second angle 114 may be two degrees. However, in other embodiments, the first angle 112 and the second angle 114 may have different values. For example, the first angle 112 may be five degrees and the second angle 114 may be forty-five degrees. Additionally or alternatively, the spectroscopy assembly 22 is configured to change the first angle 112 and/or the second angle 114, via the scanning micro-mirror 64 and/or additional mirrors that may be included in the spectroscopy assembly 22. For example, the first angle 112 may be fifteen degrees during a first portion of the flight path 14. During a second portion of the flight path 14, the first angle 112 may be adjusted (e.g., via the scanning micro-mirror 64) to five degrees. In some embodiments, the spectroscopy assembly 22 may be configured to change the first angle 112 and/or the second angle 114 in response to detection of the gas plume 20. The spectroscopy assembly 22 may decrease the first angle 112 and/or the second angle 114 to increase the resolution of the scan. However, to help detect a shape 158 of the gas plume 20, the spectroscopy assembly 22 may increase the first angle 112 and/or the second angle 114 to increase the scanning range 66.

In some embodiments, the second light beam 104 and the third light beam 108 may be offset from the first light beam 100, such that the first target area 102, the second target area 106, and the third target area 110 form a row 124 (e.g., a linear line) on the ground surface 32. Aligning the plurality of light beams 28 in the row 124 may increase the scanning range 66 and enhance an accuracy and efficiency of detection of the gas plume 20.

Figure 6:
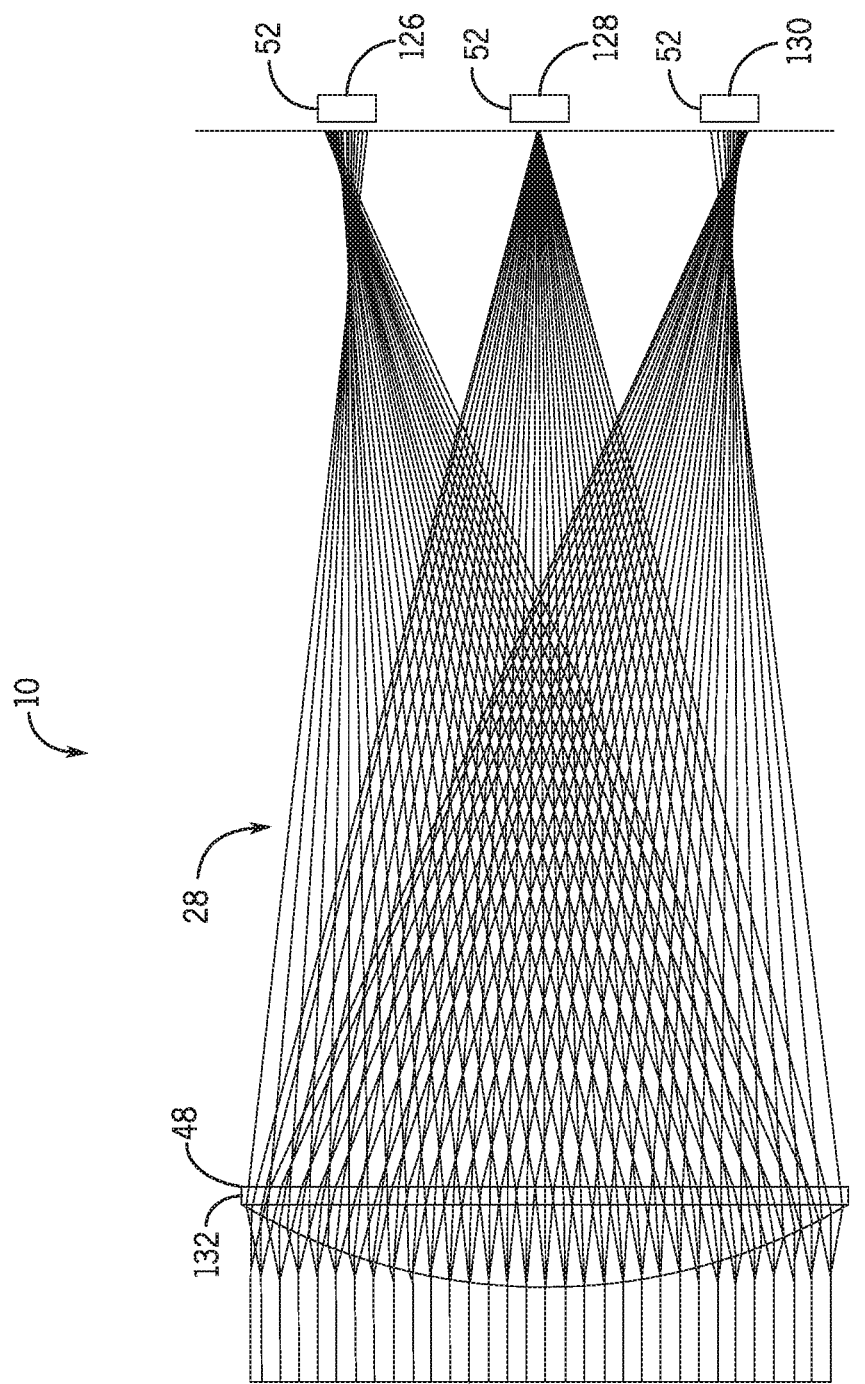
FIG. 6 is a schematic of an embodiment of a collection optic of the gas analysis system, in accordance with an aspect of the present disclosure.

FIG. 6 is a side view of an embodiment of a collection optic 48 of the gas analysis system 10. The collection optic 48 may be configured to receive each light beam 28 of the plurality of light beams 28 and direct the plurality of light beams 28 to a respective detector 52. As shown in the illustrated embodiment of FIG. 6, the collection optic 48 is configured to direct the plurality of light beams 28 to a first detector 126, a second detector 128, and/or a third detector 130. The collection optic 48 may be configured to direct a light beam 28 to one of the detectors 126, 128, 130 based at least in part on an angle of the light beam 28 with respect to the collection optic 48. The angle of the light beam 28 with respect to the collection optic 48 may correspond to an angle at which the angle was emitted from the emitter 46 of the spectroscopy assembly 22. In some embodiments, the collection optic 48 includes a condenser lens 132. The condenser lens 132 may include glass, such that the condenser lens 132 is transparent over a large wavelength range.

Alternatively, the condenser lens 132 may include a polymeric material and/or another suitable material.

In other embodiments, the collection optic 48 is a Fresnel lens. Fresnel lenses may generally be thinner than other collection optics 48, and thus, may be lighter than other optics. In still further embodiments, the collection optic 48 may be a parabolic concentrator (e.g., a Winston cone). Parabolic concentrators are generally well suited for gathering backscattered light beams 28 and redirecting the backscattered light beams 28 to the detector 52. The spectroscopy assembly 22 may include a single collection optic 48 configured to receive the plurality of light beams 28 and direct the plurality of light beams 28 to the respective detector 52. In other embodiments, the spectroscopy assembly 22 may include multiple collection optics 48 (e.g., two, three, four, five, six, seven, eight, nine, ten, or more than ten of the collection optics 48). Further, in some embodiments, the spectroscopy assembly includes multiple types of collection optics. Specifically, the spectroscopy assembly may include some combination of a condenser lens, a Fresnel lens, and/or a parabolic concentrator.

Figure 7:
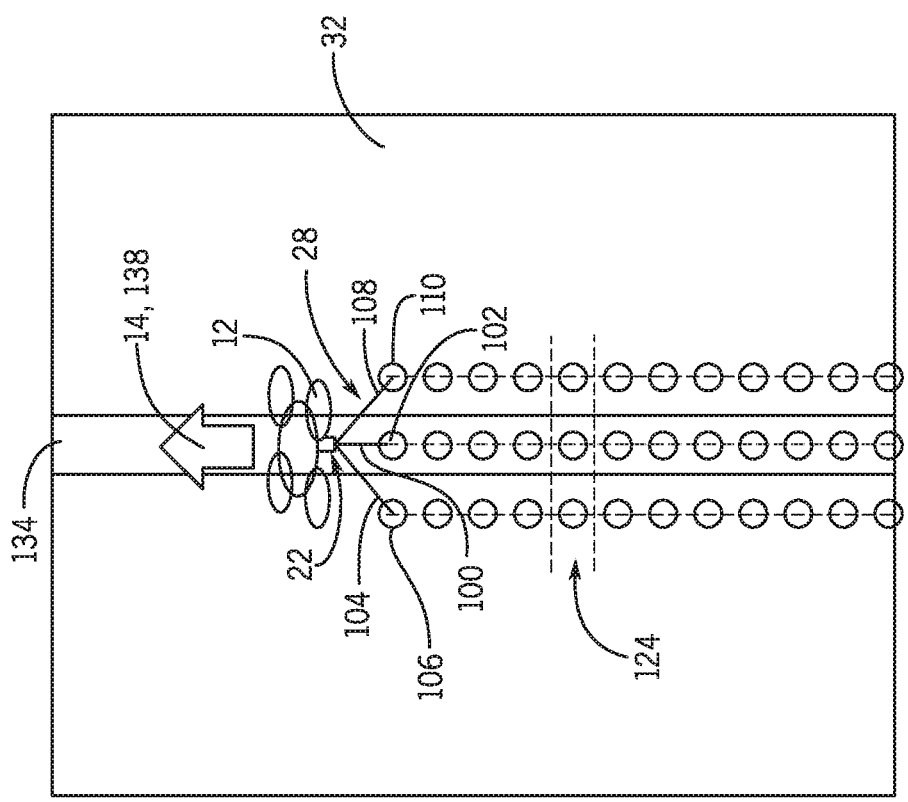
FIG. 7 is an overhead view of an operational implementation of an unmanned vehicle having the gas analysis system, in accordance with an aspect of the present disclosure.

FIG. 7 is a perspective view of an embodiment of the gas analysis system 10 having an unmanned vehicle (e.g., inspection drone 12) following the flight path 14 along a pipeline 134 (e.g., a pipeline buried beneath the ground surface 32) to detect the gas plume 20. In some embodiments, the flight path 14 may be configured to direct the unmanned vehicle 12 over the pipeline 134 to inspect the pipeline 134 for the location 18 that may be the source of the gas plume 20. The flight path 14 may be configured to follow a length of the pipeline 134. While a portion of the pipeline 134 shown in FIG. 7 is substantially linear, it should be noted that other portions of the pipeline 134 may include bends, curves, elbows, angles, or other suitable features. In some embodiments, the unmanned vehicle 12 is configured to be positioned directly above the pipeline 134 as the inspections drone travels along the length of the pipeline 134, such that the first target surface 102 includes at least a portion of the pipeline 134. In some embodiments, the first target surface 102 may include at least a portion of a surface disposed above the pipeline 134 (e.g., a ground surface 32 above a buried portion of pipeline 134).

In some embodiments, the emitters 46 are configured to emit the plurality of light beams 28 to detect the gas plume 20. As shown in the illustrated embodiment of FIG. 7, the emitters 46 are configured to emit the first light beam 100, the second light beam 104, and the third light beam 108. The second light beam 104 and the third light beam 108 are offset from the first light beam 100, such that the first target surface 102, the second target surface 106, and the third target surface 110 form the row 124 (e.g., a linear line) on the ground surface 32. As the unmanned vehicle 12 travels in a direction 138, the row 124 of target surfaces moves with respect to the unmanned vehicle 12. The first angle 112 and the second angle may be configured to position the second target surface 106 and the third target surface 110 proximate the pipeline 134. Positioning the second and third target surfaces 106, 110 proximate the pipeline 134 may increase the resolution of the scan to detect small gas plumes 20 that may be disposed between the target surfaces. Moving the target surfaces closer together (e.g., reducing the first angle 112 and the second angle 114) may increase the resolution and enable the spectroscopy assembly 22 to better detect the small gas plumes 20. The spectroscopy assembly 22 may lower the height 98 of the unmanned vehicle 12 to increase the resolution of the scan and/or utilize the scanning micromirrors 64 to reduce the first and second angles 112, 114 and improve the resolution of the scan.

Figure 8:
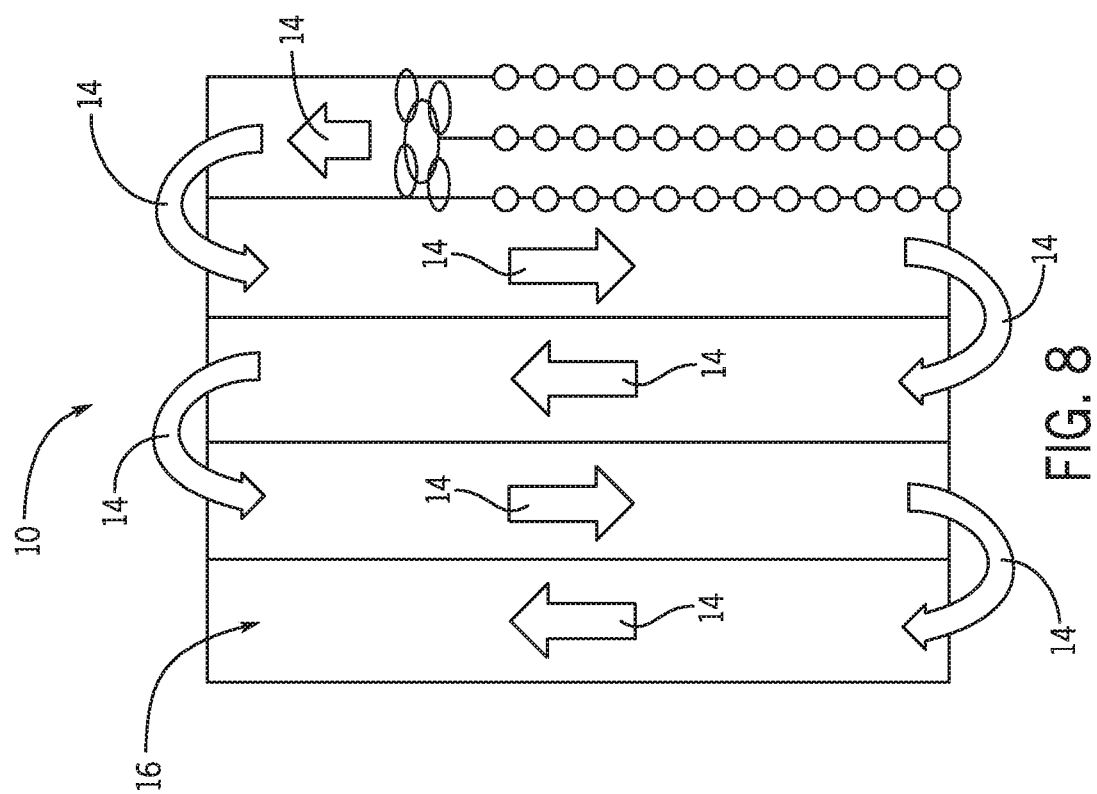
FIG. 8 is an overhead view of an embodiment of the unmanned vehicle gas analysis system, in accordance with an aspect of the present disclosure.

FIG. 8 is a perspective view of an embodiment of the gas analysis system 10 following the flight path 14 over a well pad 16 to detect a gas plume 20 at the well pad 16. A width of the well pad 16 may be too large to adequately inspect the well pad 16 with a single pass of the unmanned vehicle 12. Thus, as shown in the present embodiment, the flight path 14 may be configured to direct the unmanned vehicle 12 to traverse (e.g., move back and forth) over a span of the well pad 16 in a serpentine manner. However, the flight path 14 may be configured to follow any route suitable for directing the unmanned vehicle 12 to scan an entire area of the well pad 16.

Figure 9:
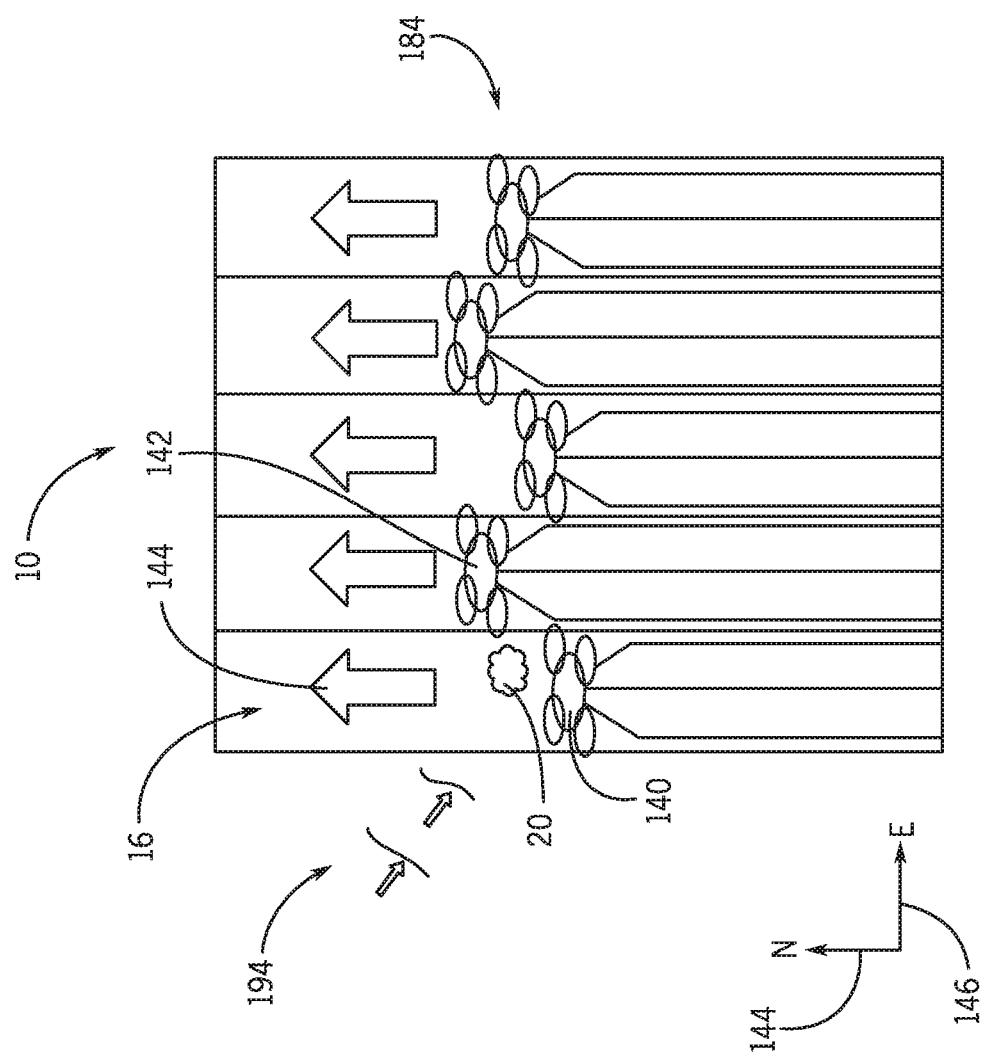
FIG. 9 is an overhead view of an operational implementation of the gas analysis system having a plurality of unmanned vehicles, in accordance with an aspect of the present disclosure.

FIG. 9 is a perspective view of an embodiment of the gas analysis system 10 having a plurality of scanning platforms 12 (e.g., inspection drones 184) following respective flight paths 14 over a well pad 16 to detect the gas plume 20. To facilitate inspection of the well pad 16, the plurality of unmanned vehicles 184 may be configured to scan the well pad 16 and cover a larger area than a single unmanned vehicle. The plurality of unmanned vehicles 184 may be configured to receive respective flight paths 14 from the user interface 92. In some embodiments, a plurality of user interfaces 92 may be configured to output the respective flight paths 14 to each of the unmanned vehicles 184. In another embodiment, each main controller 13 of the respective plurality of inspection vehicles is configured to follow a predetermined flight path 14 stored on a respective vehicle memory.

In some embodiments, the plurality of unmanned vehicles 184 are configured to scan the area of the well pad 16, such that the plurality of target surfaces corresponding to the respective unmanned vehicles 184 are oriented in the row. Orienting the target surfaces in the row along the well pad 16 may increase accuracy of a scan during gusting winds 194. For example, the plurality of unmanned vehicles 184 may include at least a first unmanned vehicle 140 and a second unmanned vehicle 142. The location 18 of the source of the gas plume 20 in the well pad 16 may be disposed along the flight path 14 of the first unmanned vehicle 140. The first and second unmanned vehicles 140, 142 may be moving in a first direction 144 along the well pad 16. The second unmanned vehicle 142 may be disposed adjacent to the first unmanned vehicle 140 with respect to a direction 146. Moreover, the second unmanned vehicle 142 may be disposed before the first unmanned vehicle 140 with respect to the direction 144 (i.e., the second unmanned vehicle 142 is ahead of the first unmanned vehicle 140). In some cases, the wind may push the gas plume 20 rapidly in the direction 146 behind the second unmanned vehicle 142 and in front of the first unmanned vehicle 140, such that the plurality of unmanned vehicles 184 may not detect the gas plume 20. Having the first unmanned vehicle 140 and the second unmanned vehicle 142 with the plurality of target surfaces in the row 124 may reduce a gap between adjacent target surfaces of respective adjacent unmanned vehicles 184.

Figure 10:
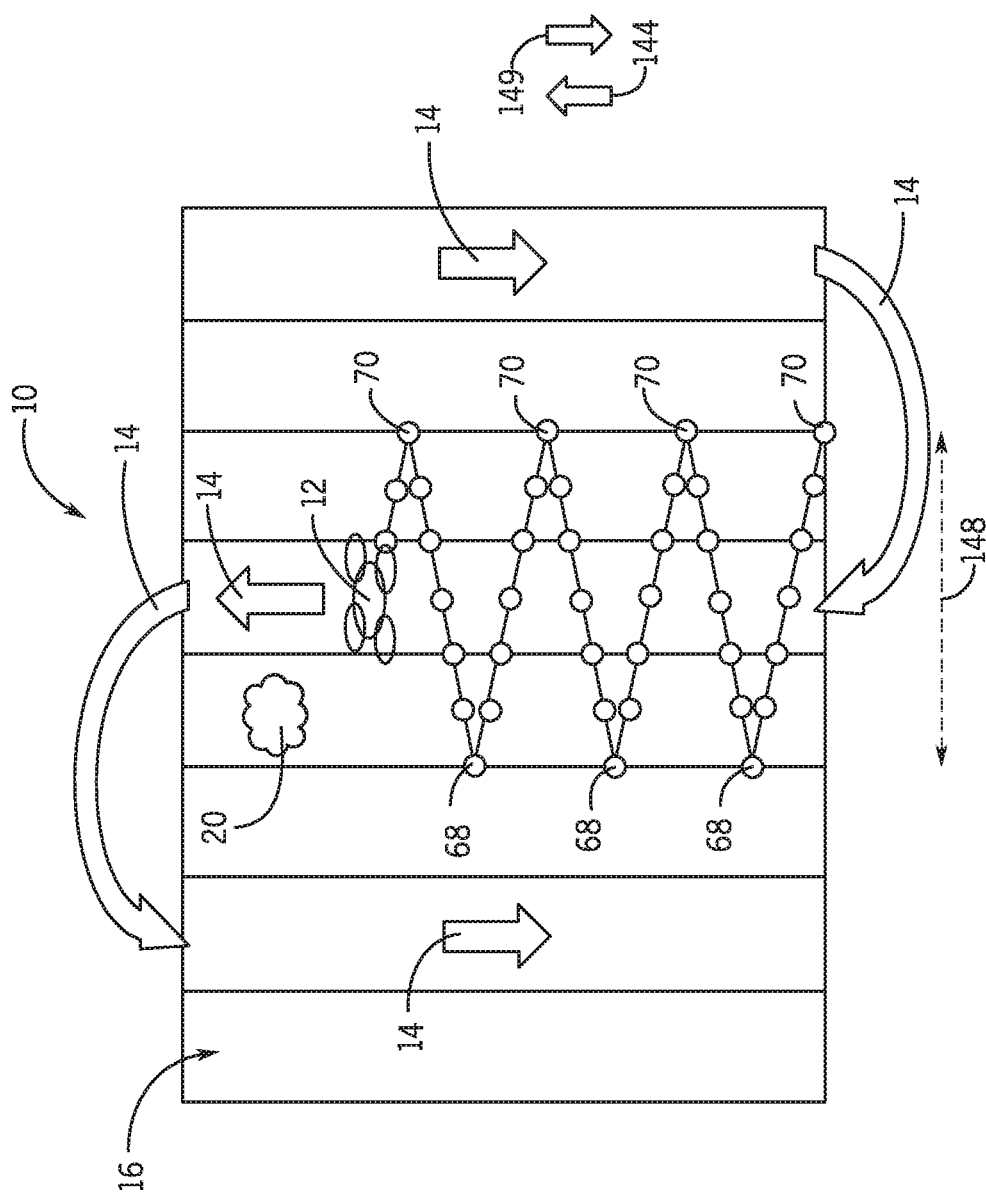
FIG. 10 is an overhead view of an operational implementation of the gas analysis system configured to sweep the light beam along the flight path, in accordance with an aspect of the present disclosure.

FIG. 10 is a perspective view of another embodiment of the gas analysis system 10 having the unmanned vehicle 12 (e.g., inspection drone) configured to sweep (e.g., oscillate or move) the light beam 28 while following the flight path 14 over the well pad 16 to detect the gas plume 20. In some embodiments, the unmanned vehicle 12 may be configured to move the emitter 46 back and forth along an axis 148 as the unmanned vehicle 12 travels in the direction 144 and a direction 149 along the flight path 14 to sweep the light beam 28 and cover a larger area of the well pad 16. For instance, sweeping the light beam may increase the range of the scan by the unmanned vehicle 12 and therefore reduce a duration in which the unmanned vehicle 12 travels along the flight path 14. The main controller 13 may cause the unmanned vehicle 12 to move back and forth along the axis 148, such that at least one light beam emitter 46 pivots back and forth between the left target surface 68 and then back to the right target surface 70.

In some embodiments, the scanning micro-mirror 64 may be configured to rotate the light beam 28 without moving the emitter 46 and/or the unmanned vehicle 12. The scanning micro-mirror 64 may direct the light beam 28 back and forth between the left target surface 68 and the right target surface 70. In some embodiments, the unmanned vehicle 12 is configured to sweep the plurality of light beams 28 to a respective left target surface 68 and back to a respective right target surface 70. Sweeping the plurality of light beams 28 may increase a breadth of the scan at the current location along the flight path 14.

Figure 11:
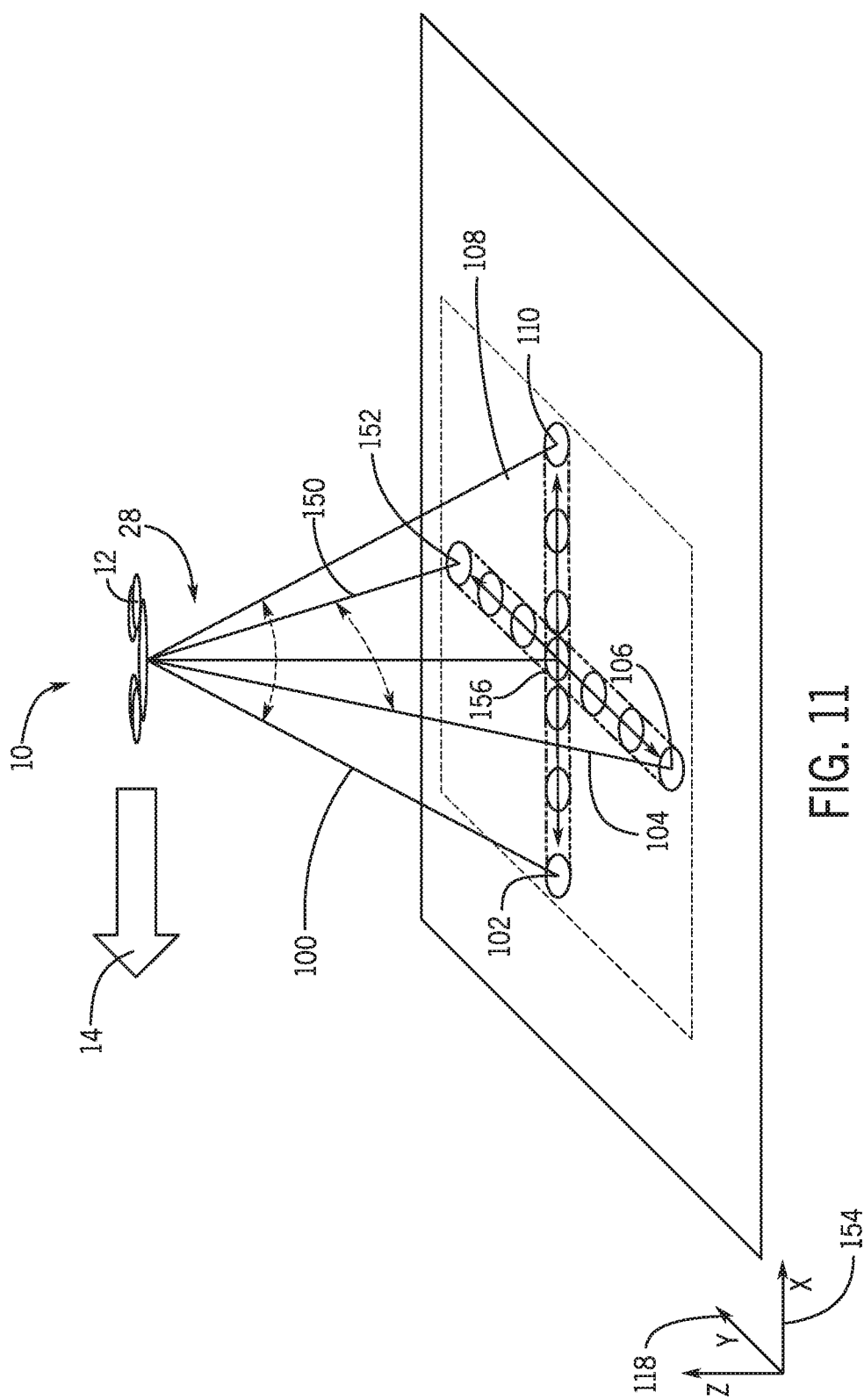
FIG. 11 is a perspective view of an operational implementation of the unmanned vehicle gas analysis system emitting one or more light beams in a multi-axis pattern, in accordance with an aspect of the present disclosure.

FIG. 11 is a perspective view of an embodiment of the gas analysis system 10 emitting a plurality of light beams 28 in a multi-planar array. In some embodiments, the unmanned vehicle 12 has the plurality of light beam emitters 46 configured to output the plurality of light beams 28 in a multi-planar array. As shown in the illustrated embodiment of FIG. 11, the unmanned vehicle 12 has the first light beam 100, the second light beam 104, the third light beam 108, and a fourth light beam 150 directed at a first target surface 102, the second target surface 106, the third target surface 110, and a fourth target surface 152 respectively. Each light beam 100, 104, 108, 150 of the plurality of light beams 28 may be offset from one another, such that their respective target surfaces 102, 106, 110, 152 are disposed at different positions. The first target surface 102 and the second target surface 106 may be offset from each other in both a first direction (e.g., an x-axis 154) and a second direction (e.g., a y-axis 118) with respect to a surface 156 (e.g., ground surface 32) disposed directly below the unmanned vehicle 12.

The gas analysis system 10 may emit the plurality of light beams 28 in a multi-planar array to detect a shape of the gas plume 20. By using light beams 28 in a multi-planar array, the gas analysis system 10 may simultaneously detect various features of the gas plume 20 along multiple axes, which may provide an indication of both a length (e.g., a distance in the y-axis 118 direction) and a width (e.g., a distance in the x-axis 154 direction) of the gas plume 20. For example, the first light beam 100 and the third light beam 108 may be offset along the x-axis 154, and the second light beam 104 and fourth light beam 150 may be offset along the y-axis 118. As a non-limiting example, the first light beam 100, the second light beam 104, and the fourth light beam 150 may detect the gas plume 20 at a first location along the flight path 14. At a second location (e.g., further along the flight path 14 in the x-direction) the second light beam 104 and the fourth light beam 150 may detect the gas plume 20, but the first light beam 100 and the third light beam 108 may not detect the gas plume 20. Further, at a third location (e.g., further still along the flight path 14 in the x-direction) the third light beam 108 may detect the gas plume 20, but the first light beam 100, the second light beam 104, and the fourth light beam 150 may not detect the gas plume 20. Thus, the controller 34 may determine that the shape 158 of the gas plume 20 is wider than the distance between the second light beam 104 and the fourth light beam 150, and narrower than the distance between the first light beam 100 and the third light beam 108. Having additional light beams 28 emitted from the unmanned vehicle 12, sweeping (e.g., rotating, oscillating, or otherwise moving) the plurality of light beams 28, and performing multiple scans proximate the detected gas plume 20 may provide additional data to identify a two-dimensional shape of the gas plume 20 with respect to the x-axis 154 and the y-axis 118.

Figure 12:
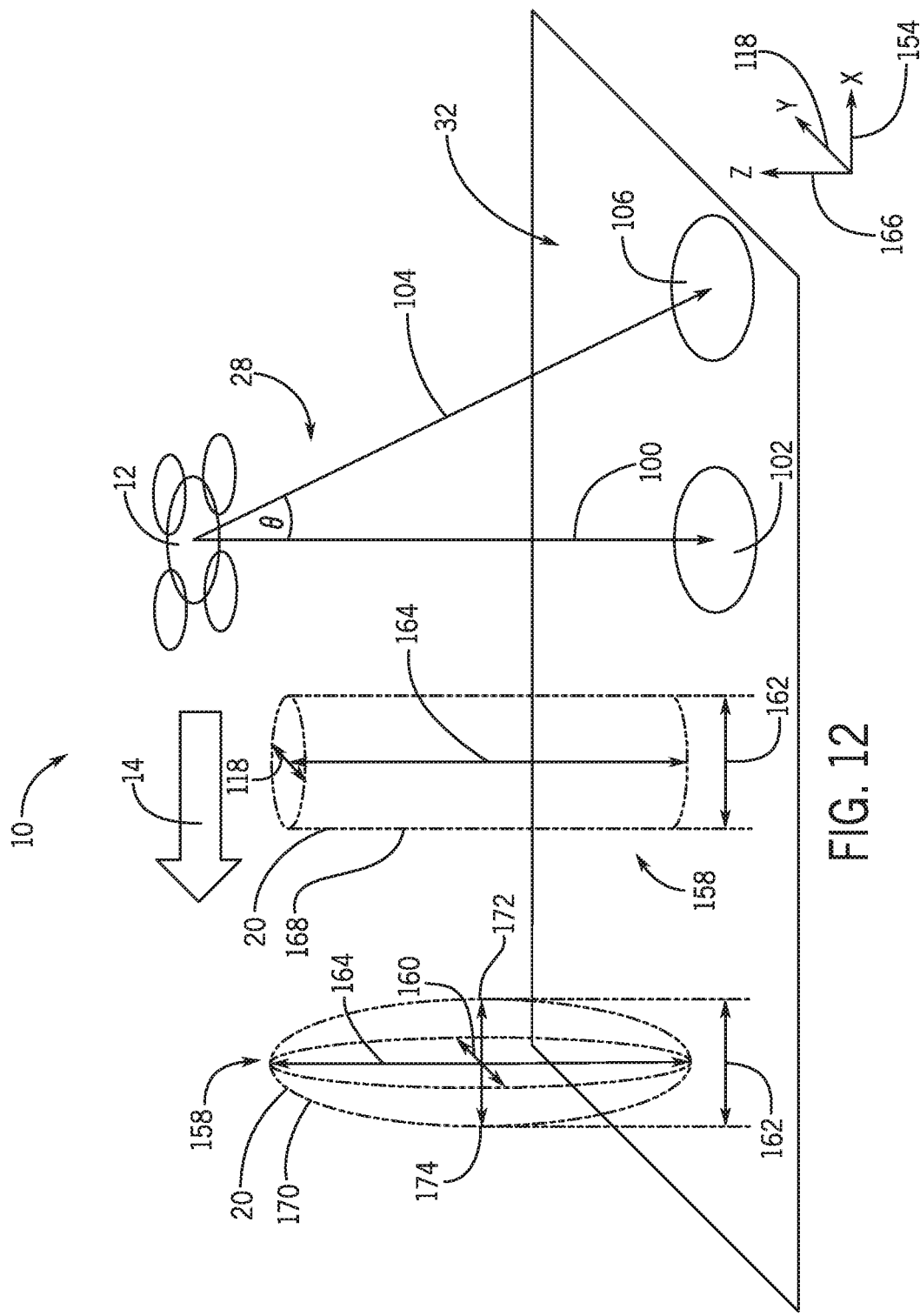
FIG. 12 is perspective view of an operational implementation of the gas analysis system emitting one or more light beams to determine classification data related to the gas plume, in accordance with an aspect of the present disclosure.

FIG. 12 is perspective view of an embodiment of the gas analysis system 10 having the unmanned vehicle 12 (e.g., inspection drone 12) emitting the plurality of light beams 28 to determine a shape 158 of the gas plume 20. For example, in addition to determining a length 160 and a width 162 of the gas plume 20, the spectroscopy assembly 22 may be configured to determine a height 164 of the gas plume 20 in a vertical direction (e.g., along a z-axis 166) to obtain further data related to the shape 158 of the gas plume 20. As shown in the illustrated embodiment of FIG. 12, both a cylindrical gas plume 168 and an elliptical gas plume 170 may be present along the flight path 14. A two-dimensional scan using the light beam 100 may determine the width 162 (e.g., along the x-axis 154) and the length 160 (e.g., along the y-axis 118) of both the cylindrical gas plume 168 and the elliptical gas plume 170. In some cases, the two-dimensional scan may indicate that the cylindrical gas plume 168 and the elliptical gas plume 170 have the same shape 158 (e.g., two-dimensional shape when viewed from above with respect to the ground surface 32).

Accordingly, the gas analysis system 10 may be configured to emit the second light beam 104 at an angle offset from the first light beam 100, which may be emitted in the downward direction, to further determine the shape 158 of the gas plume 20. For example, the first light beam 100 may be emitted toward the first target surface 102 and the second light beam 104 may be emitted toward the second target surface 106 with respect to a location of the unmanned vehicle 12. At the location of the unmanned vehicle 12, the first light beam 100 may pass through the gas plume 20 such that the gas analysis system 10 detects the gas plume 20. At a second location of the unmanned vehicle 12 (e.g., further along the flight path 14 along the x-axis 154), the unmanned vehicle may move such that the second target surface moves to the previous location of the first target surface (e.g., location of the first target surface at the first location of the unmanned vehicle). However, although the second light beam 104 is directed at the same location of the previous first target surface, the second light beam 104 may not detect the gas plume 20. In such a case, the gas plume 20 may have an elliptical shape. The first target surface 102 at the first location of the unmanned vehicle may be disposed below an edge of the elliptical shape. The first light beam 100, emitted directly downward may pass through the edge of the elliptical shape; however, the second light beam 104, which is emitted at an angle offset from the first light beam 100 may pass under the edge of the elliptical shape due to the angle of the second light beam 104 and not pass through the gas plume 20. Thus, the controller 34 may determine that the gas plume 20 has a non-uniform cross-section along the z-axis 166 (e.g., elliptical shape, spherical shape, etc.) based on the detection of the gas plume 20 by the first light beam 100 at the first location of the unmanned vehicle 12 and not detecting the gas plume 20 by the second light beam 104 at the second location of the unmanned vehicle 12. Specifically, the controller 34 may determine that the cross-section of the gas plume 20 along the z-axis 166 is smaller at a bottom portion of the gas plume 20. The controller 34 may be configured to analyze data received from the plurality of detectors over a plurality of locations of the unmanned vehicle 12 to determine a shape 158 of the gas plume 20.

Further, the spectroscopy assembly 22 may be configured to determine the shape 158 of the gas plume 20 based at least in part on a change in spectral intensity of the plurality of light beams 28 emitted via the spectroscopy assembly 22. For example, as the unmanned vehicle 12 travels along the flight path 14, the first light beam 100 may detect a lower concentration of gas proximate a first side 172 of the elliptical gas plume 170. As the unmanned vehicle 12 continues along the flight path 14, the concentration may increase to a maximum concentration of gas at a center of the gas plume 20. Further, the concentration of the elliptical gas plume 170 may decrease as the unmanned vehicle 12 moves from the center of the gas plume 20 to a second side 174 of the gas plume 20. Based on concentration data of the elliptical gas plume 170, the controller 34 may determine that a cross-section of the gas plume 20 differs along the height 164 of the gas plume 20. Thus, the controller 34 may utilize the concentration data to further characterize and analyze the shape 158 of the gas plume 20.

In some embodiments, the gas analysis system 10 is configured to determine the shape 158 of the gas plume 20 based at least in part on a change in spectral intensity of the plurality of light beams 28 emitted via the spectroscopy assembly 22 and a wind condition. For example, the wind condition may include wind blowing the gas plume 20 in a direction opposite the direction of travel of the unmanned vehicle 12 along the flight path 14. The gas plume 20 may move at substantially the same speed as the wind. For example, the wind may be blowing at five mph, and the gas plume 20 may be moving at five mph. The unmanned vehicle 12 may be moving at five mph along the flight path 14. Due to the gas plume 20 traveling in the opposite direction of the unmanned vehicle 12, the gas plume 20 may appear to have a smaller shape than an actual shape of the gas plume 20 without taking into account the wind condition. Specifically, the gas analysis system may determine that the length of the gas plume 20 is shorter than the actual length of the gas plume 20 without taking into account the wind condition. The controller 34 may be configured to account for movement of the gas plume 20 due to the wind condition when determining the shape 158 of the gas plume 20.

Figure 13:
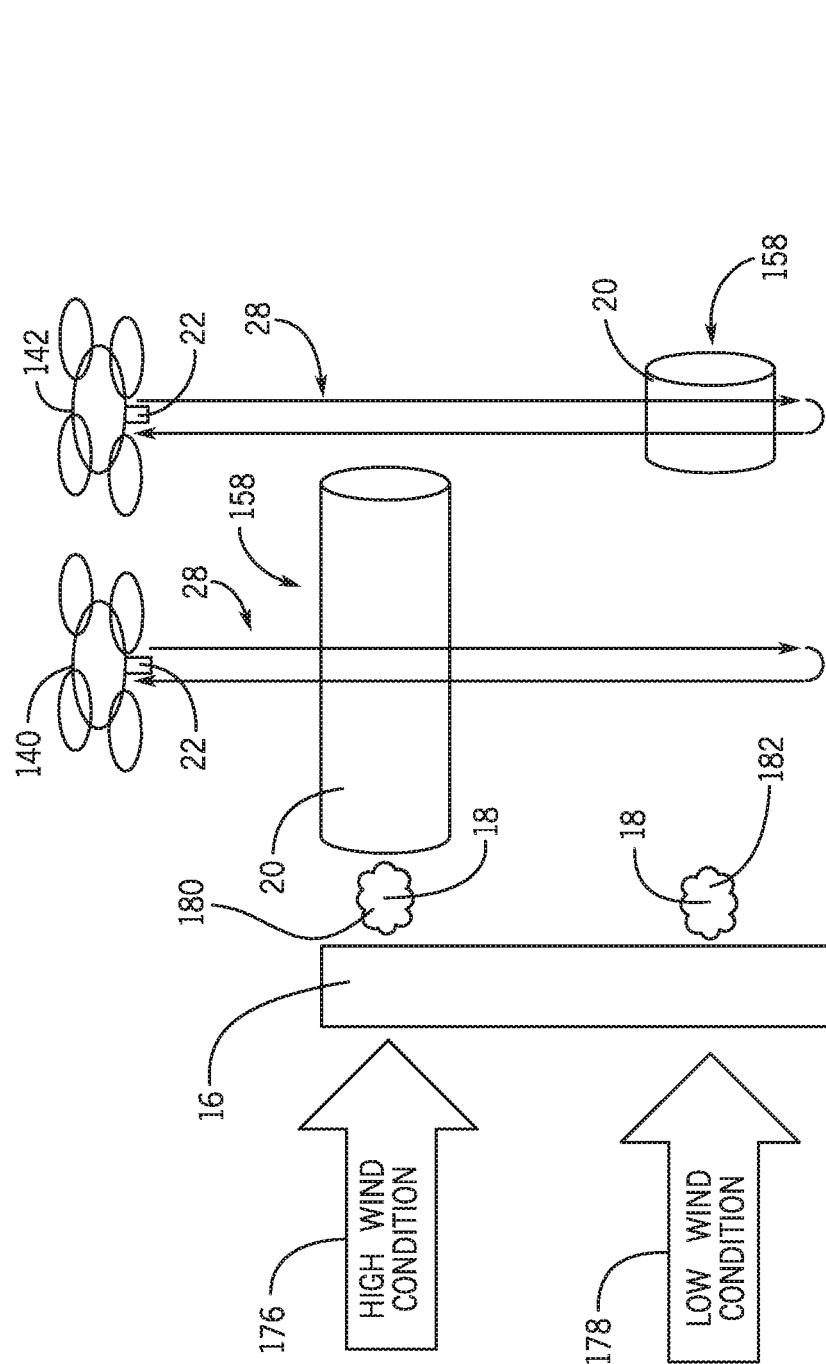
FIG. 13 is a view of an operational implementation of a plurality of unmanned vehicles analyzing the gas plume at various wind conditions, in accordance with an aspect of the present disclosure.

FIG. 13 is a perspective view of an embodiment of the first unmanned vehicle 140 inspecting the gas plume 20 in a high wind condition 176 and the second unmanned vehicle 142 inspecting the gas plume 20 in a low wind condition 178. In some embodiments, the spectroscopy assembly 22 may be configured to determine a flow rate of gas through the location 18 of the pipeline 134 and/or the well pad 16. In the present embodiment, the well pad 16 includes gas being emitted from a first location 180 and a second location 182. The first location 180 and the second location 182 may emit gas at substantially the same flow rate. For example, the first location 180 and the second location 182 may emit gas at a flow rate of fifty parts per million per minute. The high wind condition 176 may cause the gas to move away from the first location 180 faster than the low wind condition 178 may cause the gas to flow away from the second location 182. Additionally, a concentration of the gas may decrease as the gas flows further from the location 18. In some embodiments, the concentration decreases relative to a speed at which the gas flows away from the location 18. For example, gas flowing away from the location 18 at a high speed will likely have a lower concentration as compared to a gas flowing away from the location 18 at a low speed as a result of more rapid diffusion with surrounding air. Thus, the wind speed at position of the gas plume 20 may be utilized as a parameter for determining the flow rate of gas from location 18.

Moreover, the spectroscopy assembly 22 may be configured to determine a concentration of the gas plume 20. The light beam 28 may have a wavelength corresponding to an absorption frequency of the gas in the gas plume 20, such that at least a portion of the light beam 28 is absorbed as it passes through the gas plume 20. The spectroscopy assembly 22 may determine a concentration of the gas plume 20 based at least in part on a change of spectral intensity of the light beam 28 passing through the gas plume 20. For instance, the spectral intensity of a light beam 28 may decrease as a concentration of the gas plume 20 increases. Similarly, the spectral intensity of the light beam 28 may increase as a concentration of the gas plume 20 decreases. In other words, the spectral intensity of the light beam 28 and the concentration of the gas plume 20 may be inversely proportional to one another.

Further, the spectroscopy assembly 22 may determine the shape 158 of the gas plume 20 using the techniques described above. Specifically, the gas analysis system 10 may emit the plurality of light beams 28 and detect a concentration of the gas plume 20 for each light beam 28 of the plurality of light beams 28 as the unmanned vehicle 12 moves along the flight path 14 to determine the shape 158 of the gas plume 20. The controller 34 may be configured determine the gas flow rate of the gas emitted from the location 18 based at least in part on a change in the shape 158 of the gas plume 20 over time, a concentration of the gas plume 20 over a period of time, and/or the wind conditions. For example, the main controller 13 may compare the shape 158 (e.g., volumetric classification) and concentration of the gas plume 20 at a first period of time to the shape 158 and concentration of the gas plume 20 at a second period of time to determine a change in the amount of gas in the gas plume 20. Moreover, the main controller 13 may be configured to determine the gas flow rate of the gas emitted from the location 18 based at least in part on the change in the amount of gas in the gas plume 20 with respect to an amount of time elapsed between the first period of time and the second period of time.

This written description uses examples to disclose the embodiments of the present disclosure, including the best mode, and also to enable any person skilled in the art to practice the embodiments of the present disclosure, including making and using any devices or systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. A gas analysis system, comprising:
 a scanning platform configured to direct a plurality of light beams over a target area, wherein the scanning platform comprises:
  a spectroscopy assembly comprising an emitter configured to emit the plurality of light beams toward respective target surfaces of the target area, wherein the spectroscopy assembly is configured to receive a plurality of reflected light beams from the respective target surfaces and determine a spectral intensity of each reflected light beam of the plurality of reflected light beams; and a main controller configured to receive feedback from the spectroscopy assembly indicative of the spectral intensity of each reflected light beam of the plurality of reflected light beams, to determine a volumetric characterization of a gas plume based at least in part on the spectral intensity of a reflected light beam of the plurality of reflected light beams, and to determine that the volumetric characterization of the gas plume comprises a non-uniform cross-section based at least in part on a greater change in spectral intensity of a first light beam that a change of spectral intensity of a second light beam disposed adjacent to the first light beam.

2. The gas analysis system of claim 1, wherein the main controller is configured to determine a concentration of gas in the gas plume based at least in part on the volumetric characterization of the gas plume and the spectral intensity of the reflected light beam of the plurality of reflected light beams.

3. The gas analysis system of claim 1, wherein each light beam of the plurality of light beams is reflected from the respective target surface of the target area to generate a corresponding reflected light beam of the plurality of reflected light beams.

4. The gas analysis system of claim 3, wherein the spectroscopy assembly comprises a collection optic configured to receive the plurality of reflected light beams, and wherein a detector is configured to detect the spectral intensity of each reflected light beam of the plurality of reflected light beams.

5. The gas analysis system of claim 3, wherein the spectroscopy assembly comprises a plurality of emitters, and wherein each emitter of the plurality of emitters comprises an angular offset from one another, such that each light beam of the plurality of light beams is angularly offset from one another.

6. The gas analysis system of claim 5, wherein the angular offset is between 1 and 5 degrees.

7. The gas analysis system of claim 5, wherein each emitter of the plurality of emitters is oriented to direct the plurality of light beams in a line array, and wherein a distance between adjacent light beams of the plurality of light beams is based at least in part on the angular offset between the emitters.

8. The gas analysis system of claim 5, wherein the plurality of emitters is configured to emit the plurality of light beams in a multi-planar array.

9. A gas analysis system, comprising:
an unmanned aerial vehicle configured to travel along a flight path, wherein the unmanned aerial vehicle comprises:
a spectroscopy assembly configured to emit a plurality of light beams toward respective target surfaces, receive a plurality of reflected light beams, and output a spectral intensity of each reflected light beam of the plurality of light reflected beams;
a thermal imager configured to capture one or more thermal images along the flight path;
a supplemental sensor configured to detect the wind condition at a location of the unmanned aerial vehicle; and
a main controller configured to determine a location of a gas plume based at least in part on the thermal image, to determine a volumetric characterization of the gas plume based at least in part on the spectral intensity of a reflected light beam of the plurality of reflected light beams and the wind condition, to determine a concentration of a gas in the gas plume based at least in part on the volumetric characterization of the gas plume and the spectral intensity of the reflected light beam of the plurality of reflected light beams, and to determine a gas flow rate of the gas creating the gas plume based at least in part on changes in the volumetric characterization of the gas plume over time, the wind condition, the concentration of gas in the gas plume over a period of time, or any combination thereof.

10. The gas analysis system of claim 9, wherein the wind condition comprises a speed and/or a direction of wind with respect to the unmanned aerial vehicle.

11. The gas analysis system of claim 9, wherein the unmanned aerial vehicle comprises a velocity sensor configured to detect a velocity of the unmanned aerial vehicle.

12. The gas analysis system of claim 9, wherein the unmanned aerial vehicle comprises a position sensor configured to detect a position of the unmanned aerial vehicle with respect to a ground surface.

13. The gas analysis system of claim 9, wherein the unmanned aerial vehicle comprises a global positioning sensor configured to detect a current location of the unmanned aerial vehicle along the flight path.

14. A method comprising:
emitting a plurality of light beams toward a plurality of target surfaces;
reflecting each light beam of the plurality of light beams from a respective target surface of the plurality of target surfaces to generate a plurality of reflected light beams;
receiving the plurality of reflected light beams;
detecting a spectral intensity of each reflected light beam of the plurality of reflected light beams;
determining a volumetric characterization of a gas plume based at least in part on of the spectral intensity of a reflected light beam of the plurality of reflected light beams; and
determining that the volumetric characterization of the gas plume comprises a non-uniform cross-section based at least in part on a greater change in spectral intensity of a first light beam than a change of spectral intensity of a second light beam disposed adjacent to the first light beam.

15. The method of claim 14, wherein each of the plurality of light beams is angularly angular offset from each other.

16. The method of claim 14, comprising determining a location of the gas plume based at least in part on one or more thermal images received from a thermal imager.

17. The method of claim 14, comprising determining a concentration of gas in the gas plume based at least in part on the volumetric characterization of the gas plume and the spectral intensity of the reflected light beam of the plurality of reflected light beams.

* * * * *